United States Patent
Luo et al.

(10) Patent No.: US 11,421,280 B2
(45) Date of Patent: Aug. 23, 2022

(54) METHODS AND COMPOSITION FOR THE PREDICTION OF THE ACTIVITY OF ENZASTAURIN

(71) Applicant: DENOVO BIOPHARMA LLC, San Diego, CA (US)

(72) Inventors: Wen Luo, San Diego, CA (US); Hong Sun, San Diego, CA (US)

(73) Assignee: Denovo Biopharma, LLC, San Diego, CA (US)

( * ) Notice: Subject to any disclaimer, the term of this patent is extended or adjusted under 35 U.S.C. 154(b) by 522 days.

(21) Appl. No.: 16/327,788

(22) PCT Filed: Aug. 31, 2017

(86) PCT No.: PCT/US2017/049747
§ 371 (c)(1),
(2) Date: Feb. 22, 2019

(87) PCT Pub. No.: WO2018/045240
PCT Pub. Date: Mar. 8, 2018

(65) Prior Publication Data
US 2019/0233902 A1 Aug. 1, 2019

Related U.S. Application Data

(60) Provisional application No. 62/414,601, filed on Oct. 28, 2016, provisional application No. 62/382,734, filed on Sep. 1, 2016.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,668,152 A | 9/1997 | Heath et al. |
| 8,114,901 B2 | 2/2012 | Bush et al. |
| 2004/0072217 A1 | 4/2004 | Kennedy |
| 2008/0299125 A1 | 12/2008 | Hinds et al. |
| 2014/0031242 A1 | 1/2014 | Luo |
| 2015/0368720 A1 | 12/2015 | Luo |

FOREIGN PATENT DOCUMENTS

| | | |
|---|---|---|
| JP | 2014506459 A | 3/2014 |
| JP | 6440658 B2 | 12/2018 |
| WO | 0214500 A2 | 2/2002 |
| WO | 2012/106267 A1 | 8/2012 |
| WO | 2012106267 | 8/2012 |
| WO | 2012106267 A1 | 8/2012 |
| WO | 2018045240 A1 | 3/2018 |

OTHER PUBLICATIONS

Kingsmore et al. Genome-wide association studies: progress and potential fordrug discovery and development. Nature Reviews; 2008; 7: 221-230. (Year: 2008).*
Wang et al. Scientific Reports; May 2016; 6:26526: DOI: 10.1038/srep26526: p. 1-12. (Year: 2016).*
McClay et al. Molecular Psychiatry2011, 16:76-85. (Year: 2011).*
Kim et al. Blood,; 2006; 108; 8: 2720-2725. (Year: 2006).*
Cerhan et al. Genome-wide association study identifies multiple susceptibility loci for diffuse large B cell lymphoma. Nature Genetics; 2014; 46; 11: 1233-1240. (Year: 2014).*
Ghesquieres. et al. Journal of Clinical Oncology; 2015; 33:33: 3930-3937. (Year: 2015).*
Puwada et al. Cancer Genetics; 2013; 257-265. (Year: 2013).*
Butowski et al. Neuro-Oncology; 2011; 13(12): 1331-338. (Year: 2011).*
Odia et al. J Neurooncol;2016; 127:127-135, published online one Dec. 7, 2015. (Year: 2016).*
Wrensch et al. Nature Genetics; 2009; vol. 41; No. 8: 905-910. (Year: 2009).*
Communication pursuant to Article 94(3) EPC for European patent application EP17 771 623.0, dated May 25, 2021, 5 pages.
Responsive to the Communication pursuant to Article 94(3) EPC for European patent application EP17 771 623.0, dated Jun. 24, 2021, 5 pages.
Claim Amendments (marked-up version) for European patent application EP17 771 623.0, dated Jun. 24, 2021, 2 pages.
Claim Amendments (clean version) for European patent application EP17 771 623.0, dated Jun. 24, 2021, 2 pages.
Description (marked-up version ) for European patent application EP17 771 623.0, dated Jun. 24, 2021, 37 pages.
Description for European patent application EP17 771 623.0, dated Jun. 24, 2021, 34 pages.
Communication under Rule 71(3) EPC for European patent application EP17 771 623.0, dated Sep. 6, 2021, 98 pages.
Claim Amendments (marked-up version) for European patent application EP17 771 623.0, dated Nov. 19, 2021, 2 pages.
Claim Amendments (clean version) for European patent application EP17 771 623.0, dated Nov. 19, 2021, 2 pages.

(Continued)

*Primary Examiner* — Juliet C Switzer
*Assistant Examiner* — Wahwah T Johnson
(74) *Attorney, Agent, or Firm* — David. H Vance

(57) ABSTRACT

The present invention describes biomarkers that have been discovered to correlate with varied individual responses (e.g., efficacy, adverse effect, and other end points) to enzastaurin, in treating diseases such as, DLBCL, GBM, and other cancer types. The newly discovered biomarkers and others in linkage disequilibrium with them can be used in companion diagnostic tests which can help to predict drug responses and apply drugs only to those who will be benefited, or exclude those who might not be beneficial, by the treatment.

20 Claims, 16 Drawing Sheets
Specification includes a Sequence Listing.

(56) References Cited

OTHER PUBLICATIONS

Description (marked-up version) for European patent application EP17 771 623.0, dated Nov. 19, 2021, 13 pages.
Description (clean version) for European patent application EP17 771 623.0, dated Nov. 19, 2021, 13 pages.
Responsive to the Communication under Rule 71(3) EPC for European patent application EP17 771 623.0, dated Nov. 19, 2021, 2 pages.
Response to Office Action for Indonesia patent application ID 00201901652, dated Aug. 1, 2021, 10 pages.
Figures in Response to Office Action for Indonesia patent application ID 00201901652, dated Aug. 1, 2021, 16 pages.
Description (clean version) for Indonesia patent application ID 00201901652, dated Aug. 1, 2021, 92 pages.
2nd Office Action for Indonesia patent application ID 00201901652, dated Nov. 3, 2021, 2 pages.
2nd Office Action (Englis version) for Indonesia patent application ID 00201901652, dated Nov. 3, 2021, 2 pages.
1st Examination Report for Indian patent application IN201917006962, dated Mar. 31, 2021, 8 pages.
Response to 1st Examination Report for Indian patent application IN201917006962, dated Dec. 20, 2021, 24 pages.
Claims (marked-up version) for Indian patent application IN201917006962, dated Dec. 20, 2021, 18 pages.
Abstract for Saudi Arabia patent application SA519401228, dated Sep. 16, 2021, 1 page.
Arguments for Saudi Arabia patent application SA519401228, dated Sep. 16, 2021, 24 pages.
Claims for Saudi Arabia patent application SA519401228, dated Sep. 16, 2021, 6 pages.
Detailed Description for Saudi Arabia patent application SA519401228, dated Sep. 16, 2021, 112 pages.
1st Examination Report for Saudi Arabia patent application SA519401228, dated Nov. 13, 2021, 6 pages.
1st Examination Report (English version) for Saudi Arabia patent application SA519401228, dated Nov. 13, 2021, 6 pages.
Office Action for Thailand patent application TH1901001255, dated May 18, 2021, 3 pages.
Response to Office Action for Thailand patent application TH1901001255, dated Aug. 9, 2021, 118 pages.
Official Action for Japanese patent application JP2020-142358, dated Oct. 1, 2021, 2 pages.
Arguments for Japanese patent application JP2020-142358, dated Dec. 28, 2021, 1 pages.
International Search Report for international patent application PCT/US2017/049747, dated Nov. 7, 2017, 6 pages.
International Preliminary Report on Patentability for international patent application PCT/US2017/049747, dated Mar. 5, 2019, 10 pages.
Written Opinion of the International Searching Authority for international patent application PCT/US2017/049747, dated Mar. 5, 2019, 9 pages.
Communication pursuant to Rules 161(1) and 162 EPC for European patent application EP17771623.0, dated Apr. 9, 2019, 3 pages.
Response to Communication pursuant to Rules 161(1) and 162 EPC for European patent application EP17771623.0, dated Oct. 18, 2019, 43 pages.
Communication pursuant to Article 94(3) EPC for European patent application EP17771623.0, dated Dec. 16, 2019, 6 pages.
Response to the Communication pursuant to Article 94(3) EPC for European patent application EP17771623.0, dated Jun. 25, 2020, 11 pages.
Claim Amendments (marked-up version) in response to the Communication pursuant to Article 94(3) EPC for European patent application EP17771623.0, dated Jun. 25, 2020, 6 pages.
Claim Amendments (clean version) in response to the Communication pursuant to Article 94(3) EPC for European patent application EP17771623.0, dated Jun. 25, 2020, 5 pages.
New experimental data in response to the Communication pursuant to Article 94(3) EPC for European patent application EP17771623.0, dated Jun. 25, 2020, 1 page.
Communication pursuant to Article 94(3) EPC for European patent application EP17771623.0, dated Nov. 13, 2020, 5 pages.
Claim Amendments (marked-up version) in response to the Communication pursuant to Article 94(3) EPC for European patent application EP17771623.0, dated Mar. 18, 2021, 5 pages.
Claim Amendments (clean version) in response to the Communication pursuant to Article 94(3) EPC for European patent application EP17771623.0, dated Mar. 18, 2021, 2 pages.
Response to the Communication pursuant to Article 94(3) EPC for European patent application EP17771623.0, dated Mar. 18, 2021, 7 pages.
Notification prior to examination for Israeli patent application IL264996, dated Feb. 16, 2020, 7 pages.
McNulty et al., "Enzastaurin (LY317615.HCI) enhances the efficacy of multiple anti-angiogenic agents, targeted therapies and standard oncolytics," 99th AACR Annual Meeting—Apr. 12-16, 2008; San Diego, CA American Association for Cancer Research, 4 pages, Abstract https://cancerres.aacrjournals.org/content/68/9_Supplement/LB-104.
Neri et al., "The oral protein-kinase C beta inhibitor enzastaurin (LY317615) suppresses signaling through the AKT pathway, inhibits proliferation and induces apoptosis in multiple myeloma cell . . . ," Leukemia & Lymphoma, Jul. 2008; 49(7): 1374-1383 DOI: 10.1080/10428190802078289.
Parsons et al., "Enzastaurin (LY317615.HCI) dramatically enhances the sensitivity of glioblastoma cells and xenografts to temozolomide by blocking signaling through the p90RSK and the AKT pathways and inhibiting CREB transcription actor activation," 99th AACR Annual Meeting—Apr. 12-16, 2008; San Diego, CA, American Association for Cancer Research, 4 pages, Abstract https://cancerres.aacrjournals.org/content/68/9_Supplement/LB-117.
Rossi et al., "The PKCβ Selective Inhibitor, Enzastaurin (LY317615), Inhibits Growth of Human Lymphoma Cells," Blood (2005) 106 (11): 1483, 5 pages, Abstract https://doi.org/10.1182/blood.V106.11.1483.1483.
Tabatabai et al., "Synergistic antiglioma activity of radiotherapy and enzastaurin," Jan. 9, 2007, Annals of Neurology / vol. 61, Issue 2 / p. 153-161, Abstract https://doi org/10.1002/ana.21057.
1st Office Action for Thailand patent application TH1901001255, dated May 18, 2021, 3 pages.
Butowski et al., "Phase II and pharmacogenomics study of enzastaurin plus temozolomide during and following radiation therapy in patients with newly diagnosed glioblastoma multiforme and gliosarcoma," Neuro-Oncology 13 (12):1331-1338, 2011 doi:10.1093/neuonc/nor130.
Deissler et al., "Protein kinase C inhibitor," ScienceDirect, 2010, p0088-0119.
Denovo Biomarkers Homepage11, Sep. 16, 2014 (Sep. 16, 2014), XP055418256, Retrieved from the Internet: URL:http://www.denovobiopharma.com/Denovo_ Lilly News.html, 1 page.
Driton et al., "Efficacy of Larotrectinib in TRK Fusion-Positive Cancers in Adults and Children," N Engl J Med Feb. 22, 2018; 378(8): 731-739 doi:10.1056/NEJMoal714448.
Dudek et al., "Protein kinase C-beta inhibitor enzastaurin (LY317615. HCL) enhances radiation control of murine breast cancer in an orthotopic model of bone metastasis," Investigational new Drugs, Sep. 5, 2007, 26(1):13-24 https://link.springer.com/article/10.1007/s10637-007-9079-y.
Dudek et al., "Genomics of Signaling Crosstalk of Estrogen Receptor a in Breast Cancer Cells," PLoS One. 2008; 3(3): e1859, 22 pages doi: 10.1371/journal.pone.0001859.
Graff et al., "The Protein Kinase CB-selective Inhibitor, Enzastaurin (LY317615.HCI), Suppresses Signaling through the AKT Pathway, Induces Apoptosis, and Suppresses Growth of Human Colon Cancer and Glioblastoma Xenografts," Cancer Res 2005; 65: (16). Aug. 15, 2005 doi:10.1158/0008-5472.CAN-05-0071.
Hao et al., "LdCompare: rapid computation of single-and multiple-marker r2 and genetic coverage," Bioinformatics Applicaion Note, vol. 23 no. 2 2007, pp. 252-254 doi:10.1093/bioinformatics/btl574.

(56) References Cited

OTHER PUBLICATIONS

Ihmc, "A haplotype map of the human genome," Nature, Oct. 27, 2005, vol. 437, 0044-0119 dio:10.1038/nature04226.
Jergenson, "A paradigm shift in biomarker guided oncology drug development," Ann Transl Med 2019;7(7):148, 0066-0119 doi:10.21037/atm.2019.03.36.
Korn et al., "Integrated genotype calling and association analysis of SNPs, common copy number polymorphisms and rare CNCs," Nat Genet. Oct. 2008; 40(10): 1253-1260 doi: 10.1038/ng.237.
Kuo et al., "Efficacy of the Multi-Kinase Inhibitor Enzastaurin is Dependent on Cellular Signaling Context," Mol Cancer Ther. Oct. 2010; 9(10): 2814-2824 doi:10.1158/1535-7163.MCT-10-0352.
McLeod et al., "Selection of Markers to Predict Tumour Response Or Survival: Description of a Novel Approach," European Journal of Cancer, vol. 35, No. 12, pp. 1650-1652, 1999.
Moreau et al., "Protein kinase C inhibitor enzastaurin induces in vitro and in vivo antitumor activity in Waldenstrom macroglobulinemia," Blood, Jun. 1, 2007, vol. 109, No. 11, p. 4964-4972 DOI 10.1182/blood-2006-10-054577.
Parsons et al., "Enzastaurin (LY317615.HCL) dramatically enhances the sensitivity of glioblastoma cells and xenografts to temozolomide by blocking signaling through the p90RSK and the AKT pathways and inhibiting CREB transcription factor activation," AACR Annual Meeting—Apr. 12-16, 2008, 2 pages.
Podar et al., "Targeting PKC in multiple myeloma: in vitro and in vivo effects of the novel, orally available small-molecule inhibitor enzastaurin (LY317615.HCI)," Blood, Feb. 15, 2007 vol. 109, No. 4, p. 1669-1677 DOI 10.1182/blood-2006-08-042747.
Querfeld et al., "The Selective Protein Kinase C B Inhibitor Enzastaurin Induces Apoptosis in Cutaneous T-Cell Lymphoma Cell Lines through the AKT Pathway," Journal of Investigative Dermatology (2006) 126, 1641-1647 doi:10.1038/sj.jid.5700322.
Rabee et al., "A genotype calling algorithm for affymetrix SNP arrays," Bioformatics Original Paper, vol. 22 No. 1 2006, pp. 7-12 doi:10.1093/bioinformatics/bti741.
Rizvi et al., "Enzastaurin (LY317615), a protein kinase CB inhibitor, inhibits the AKT pathway and induces apoptosis in multiple myeloma cell lines," Mol Cancer Ther 2006;5(7). Jul. 2006, p. 1783-1789 doi:10.1158/1535-7163.MCT-05-0465.
Rizvi et al. "A Phase I study of LGD 1069 in Adults with Advanced Cancer," Clin Cancer Res ( 1999 ) 5 : 1658-1664.
Rossi et al., "The PKCB Selective Inhibitor, Enzastaurin (LY317615), Inhibits Growth of Human Lymphoma Cells," Blood (2005) 106 (11): 1483 https://doi.org/10.1182/blood.V106.11.1483.1483.
Database: rs30960411,Oct. 24, 2017 (Oct. 24, 2017), XP055418271, Retrieved from the Internet: URL:https://alfred.med.yale.edu/alfred/rec ordinfo.asp?condition=sites.site -uid= 'SI37 5338D [retrieved on Oct. 24, 2017] the whole document.
Database:rs30960511, Oct. 24, 2017 (Oct. 24, 2017), XP055418275, Retrieved from the Internet: URL:https://alfred.med.yale.edu/alfred/rec ordinfo.asp?condition=sites.site -uid= 'SI37 5339E [retrieved on Oct. 24, 2017] the whole document.
Spalding et al., "Inhibition of Protein Kinase CB by Enzastaurin Enhances Radiation Cytotoxicity in Pancreatic Cancer," Clin Cancer Res 2007;6827 13(22) Nov. 15, 2007, p. 6827-6833 doi:10.1158/1078-0432.CCR-07-0454.
Vincent et al., "Biomarkers that currently affect clinical practice: EGFR, ALK, MET, KRAS," Jun. 2012Current Oncology 19(Suppl 1):S33-44 DOI:10.3747/co.19.1149.
West et al., "Activation of the PI3K/Akt pathway and chemotherapeutic resistance Kip A. West, S. Sianna Castillo Castillo, Phillip A. Dennis," Drug Resistance Updates 5 (2002) 234-248.
Request for Standard Examination for Australian patent application AU2017318669, dated Aug. 3, 2021, 33 pages.
The Request for the Examination and the Amendments for Brazil patent application BR1120190039511, dated Aug. 3, 2020, 117 pages.
Notice of Reason for Rejection for Japanese patent application JP2019-512609, dated Oct. 4, 2021, 4 pages.
Notice of Reason for Rejection (English version) for Japanese patent application JP2019-512609, dated Oct. 4, 2021, 11 pages.
Requesting Full Examination for Malaysia Patent Application No. MYPI2019001111, dated Aug. 26, 2021, 1 page.
Office Action for Russian patent application RU2019109011, dated Aug. 26, 2020, 7 pages.
Office Action (English version) for Russian patent application RU2019109011, dated Aug. 26, 2020, 5 pages.
Response to Office Action for Russian patent application RU2019109011, dated Jan. 22, 2021, 2 pages.
Search Report for Russian patent application RU2019109011, dated Jan. 22, 2021, 2 pages.
Amended Claims (clean version) for Russian patent application RU2019109011, dated Nov. 19, 2021, 16 pages.
Amended Claims (marked-up version) for Russian patent application RU2019109011, dated Nov. 19, 2021, 16 pages.
Amended Claims (clean version) for Russian patent application RU2019109011, dated Nov. 19, 2021, 12 pages.
Response to Office Action for Russian patent application RU2019109011, dated Nov. 19, 2021, 1 page.
Examination Request for Singapore patent application SG10201912134T, dated Oct. 22, 2021, 99 pages.
Amendments for Singapore patent application SG10201912134T, dated Oct. 22, 2021, 23 pages.
Office Action for Taiwan patent application TW106129838, dated Jun. 17, 2021, 9 pages (and English Translation of the Office Action, 5 pages).
Search Report (English version) forTaiwan patent application TW106129838, dated Jun. 17, 2021, 1 page.
Response to Office Action for Taiwan patent application TW106129838, dated Dec. 21, 2021, 9 pages.
Amended Claims for Taiwan patent application TW106129838, dated Dec. 21, 2021, 3 pages.
"Denovo Biopharma Acquires Late-Stage Oncology Drug From lilly For Development As A Personalized Medicine," Denovo Biomarkes Homepage, dated Sep. 16, 2014, 1 page.
Dubois et al., "Next-Generation Sequencing in Diffuse Large B-Cell Lymphoma Highlights Molecular Divergence and Therapeutic Opportunities: a LYSA Study," Clin Cancer Res 2016;22:2919-2928. Published OnlineFirst Jan. 27, 2016 doi:10.1158/1078-0432.CCR-15-2305.
Scholtysik et al., "Characterizatin of genomic imbalances in diffuse large B-cell lymphoma by detailed SNP-chip analysis," Int. J. Cancer: 136, 1033-1042 (2015) DOI: 10.1002/ijc.29072.
Written Request for Examination of Application for Korean patent application KR10-2019-7009407, dated Aug. 25, 2020, 73 pages.
Preliminary Examination-Clear Formalities Report for Malaysia patent application PI2019001111, dated Jul. 14, 2020, 2 pages.
Notice of Entering the National Phase (Section 780 of Patents ACT 1983) for Malaysia patent application PI2019001111, dated Jul. 14, 2020, 2 pages.
Office Action for Russian patent application RU2019109011/10(017261), dated Jan. 22, 2021, 7 pages with extra 5 pages of English language equivalent or summary.
Search Report for Russian patent application RU2019109011/10(017261), dated Jan. 22, 2021, 2 pages with extra 2 pages of English language equivalent or summary.
Request for Examination for Vietnam patent application VT???1-2019-01496, dated Feb. 27, 2020, 4 pages.
Request for Valuntary Amendments and Amended Claims for Vietnam patent application VT??1-2019-01496, dated Feb. 27, 2020, 6 pages.
Amended Claims for Japanese patent application JP2019-512609, dated Aug. 26, 2020, 21 pages.
Filing Petition for Japanese patent application JP2019-512609, dated Aug. 26, 2020, 2 pages.
Filing a Voluntary Amendment for Japanese patent application JP2019-512609, dated Aug. 26, 2020, 15 pages.
Request for Examination for Japanese patent application JP2019-512609, dated Aug. 26, 2020, 1 page.
Examination Report for Indian patent application IN201917006962, dated Mar. 31, 2021, 8 pages.

(56) References Cited

OTHER PUBLICATIONS

Office Action for Kekayaan patent application P00201901652-TA, dated Mar. 1, 2021, 2 pages with extra 2 pages of English language equivalent or summary.
Office Action for Argentina Patent Application ARP170102447, dated Jan. 6, 2022, 5 pages with extra 2 pages of English language equivalent or summary.
Response to 2nd Office Action for Indonesia Patent Application ID P-00201901652, dated Feb. 18, 2022, 3 pages.
Description in response to 2nd Office Action for Indonesia Patent Application ID P-00201901652, dated Feb. 18, 2022, 97 pages.
Figures in response to 2nd Office Action for Indonesia Patent Application ID P-00201901652, dated Feb. 18, 2022, 16 pages.
Amended Claims filed with the JPO for Japanese Patent Application JP2019-512609, dated Mar. 11, 2022, 9 pages.
Amendment as filed for Japanese Patent Application JP2019-512609, dated Mar. 11, 2022, 3 pages.
Argument as filed for Japanese patent application JP2019-512609, dated Mar. 11, 2022, 11 pages.
Office Action for Russian Patent Application RU2019109011, dated Jan. 18, 2022, 4 pages with extra 2 pages of English language equivalent or summary.
Response to Office Action for Russian Patent Application RU2019109011, dated Mar. 28, 2022, 1 page.
Amended Claims as filed in response to Office Action for Russian Patent Application RU2019109011, dated Mar. 28, 2022, 7 pages with extra 7 pages of English language equivalent or summary.
Amended Claims (Marked) for Russian Patent Application RU2019109011, dated Mar. 28, 2022, 7 page.
Communication under Rule 71(3) EPC for European Patent Application EP17 771 623.0, dated Mar. 4, 2022, 98 pages.
Response to the Communication under Rule 71(3) EPC for European Patent Application EP17 771 623.0, dated Mar. 25, 2022, 2 pages.
Final Office Action for Japanese Patent Application JP2020-142358, dated Mar. 17, 2022, 1 page.
2nd Examination Report for Saudi Arabia Patent Application SA519401228, dated Jan. 22, 2022, 5 pages with extra 3 pages of English language equivalent or summary.

\* cited by examiner

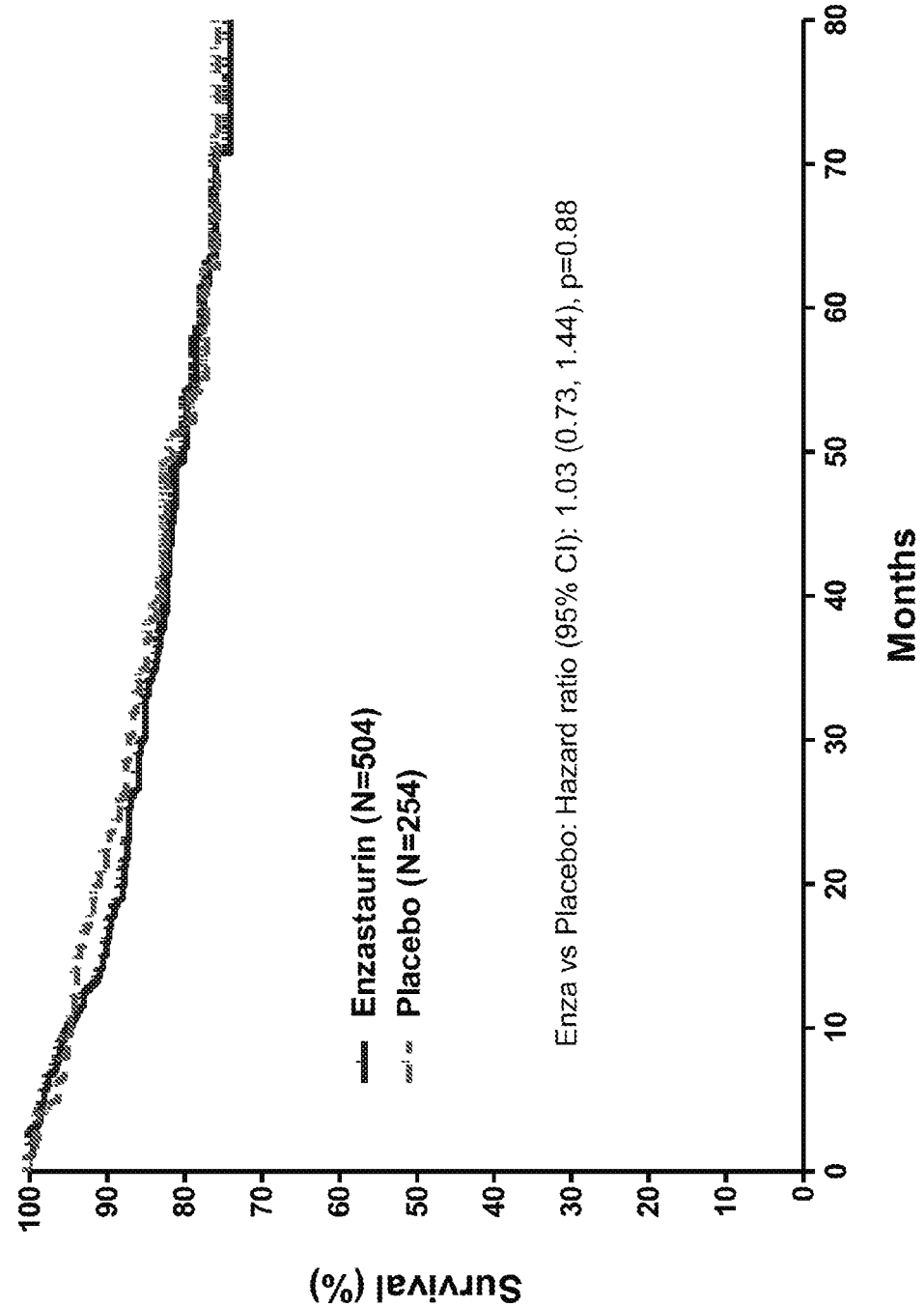

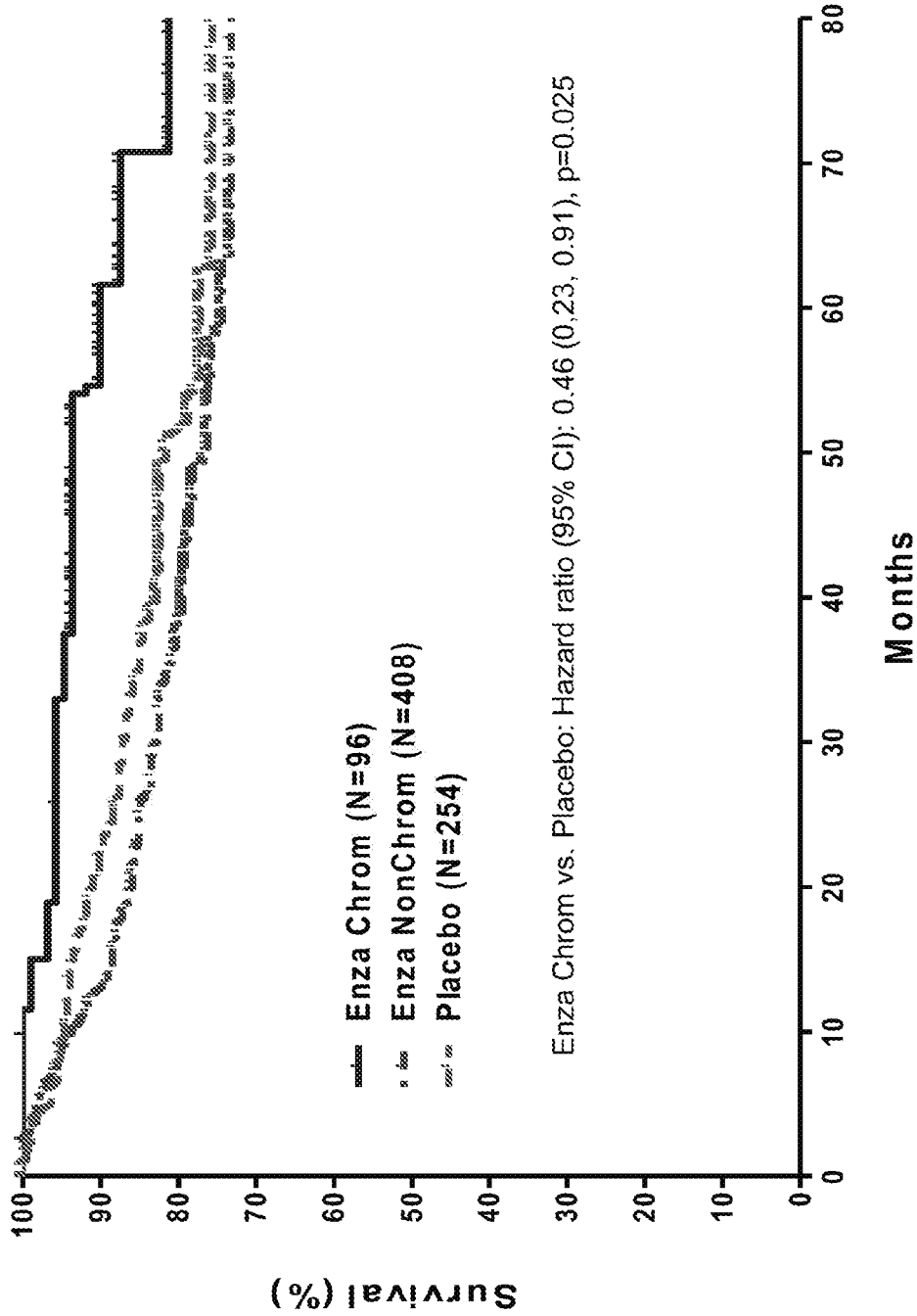

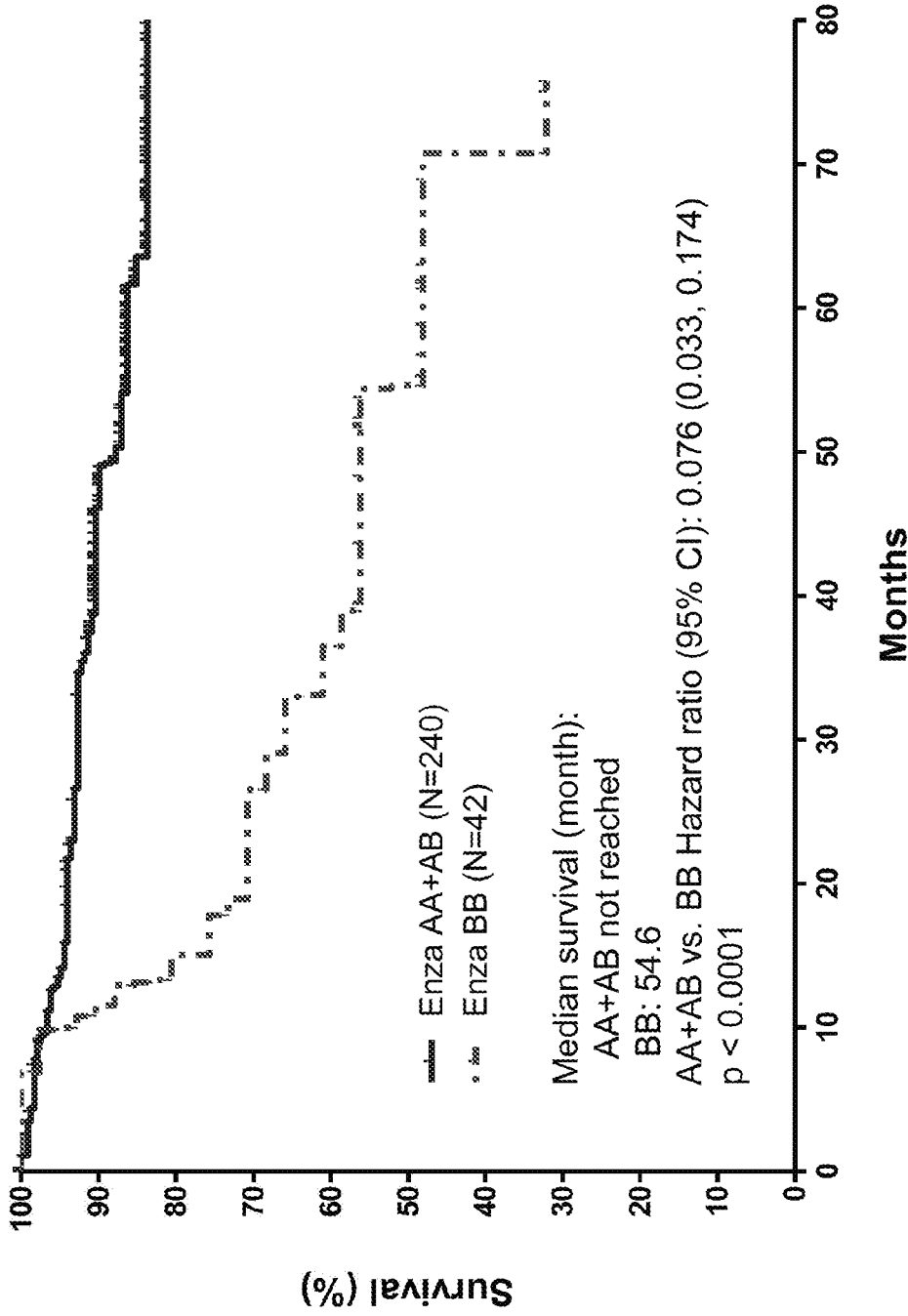

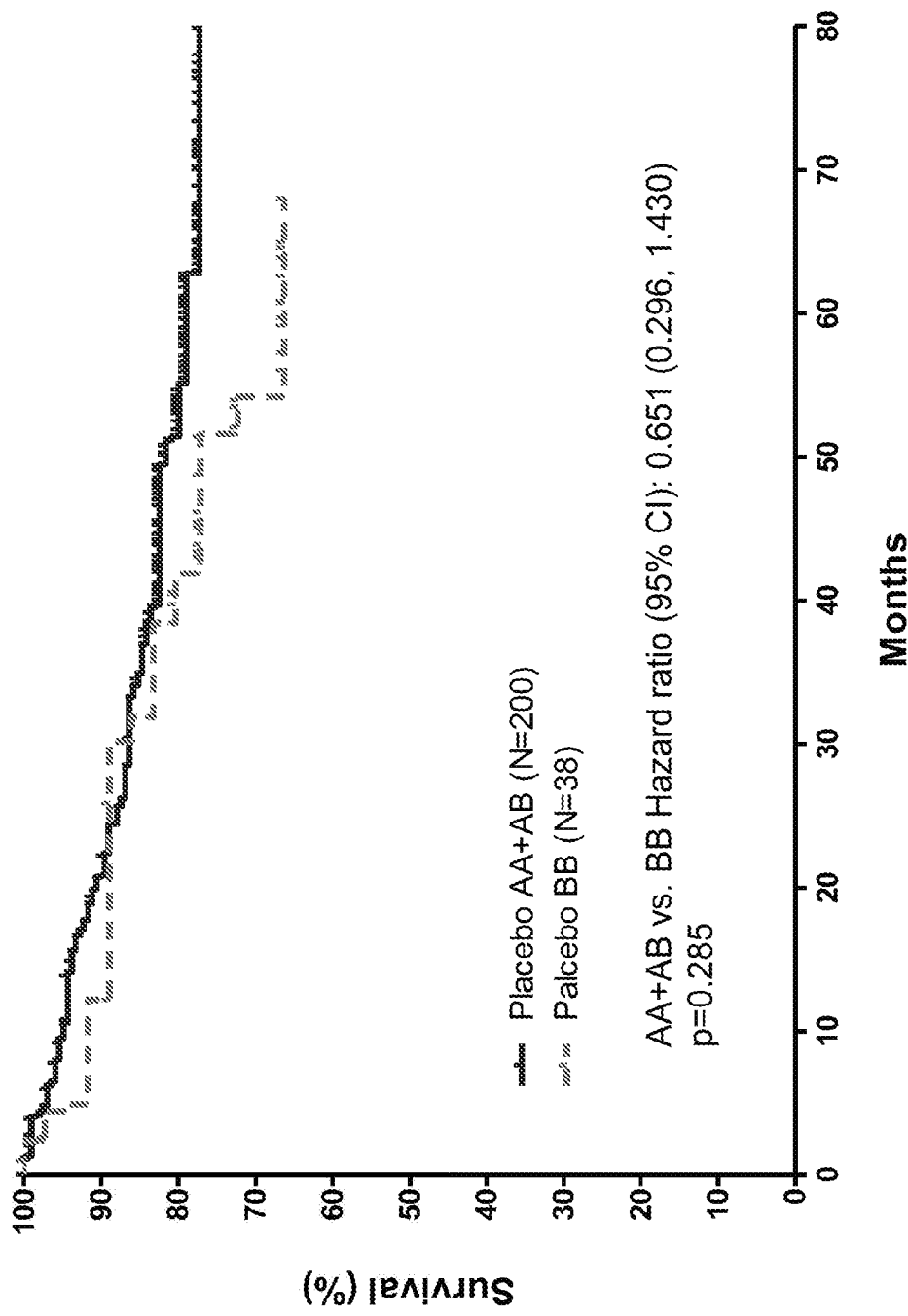

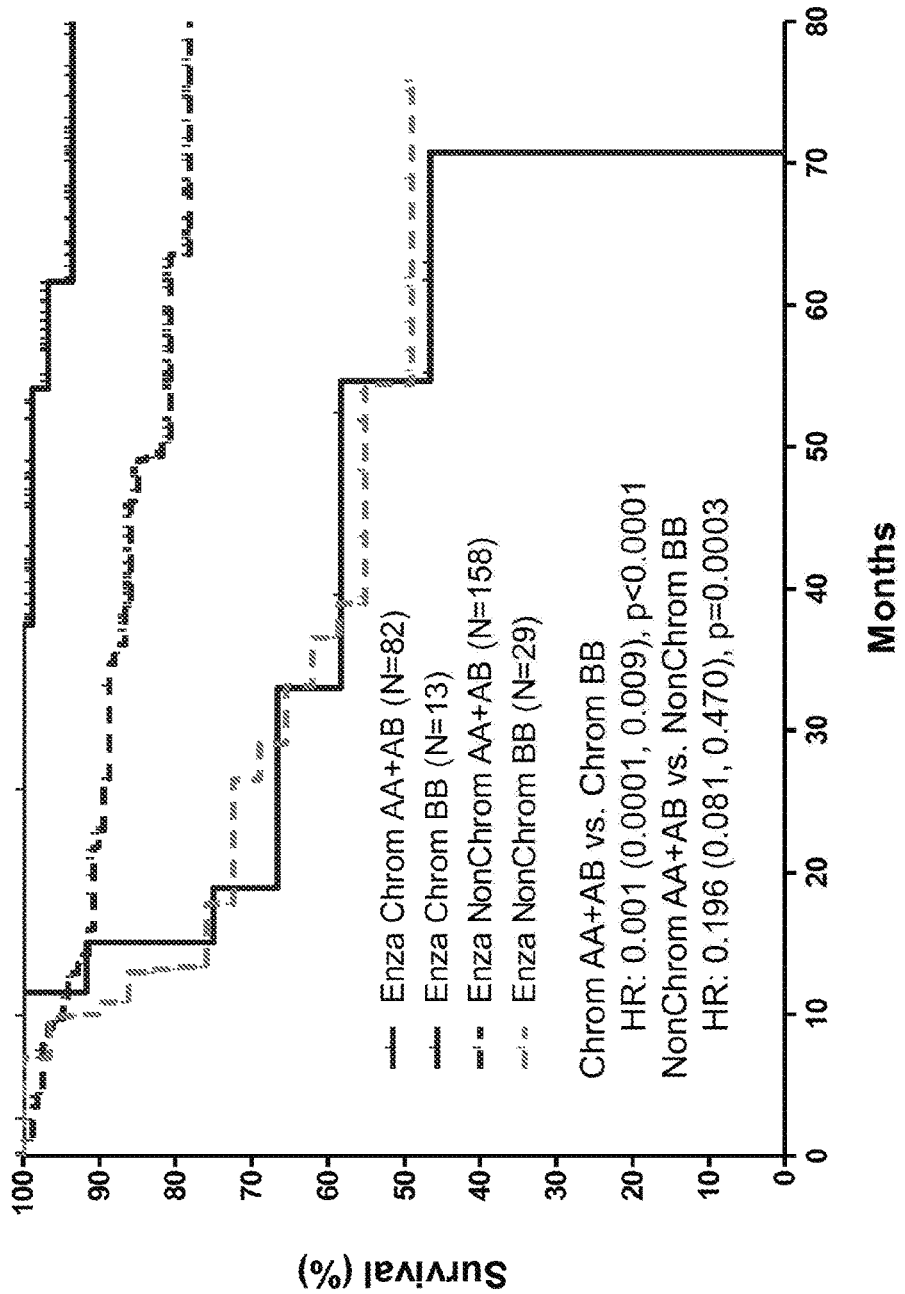

Phase II 1st Line RCHOP + Enzastaurin vs. RCHOP in intermediate & high risk DLBCL

- Complete restaging was performed at the end of Cycle 6, and responses were categorized according to the International Working Group (IWG) criteria, 1999
- Maintenance therapy was continued in Arm A with response evaluated every 8 weeks

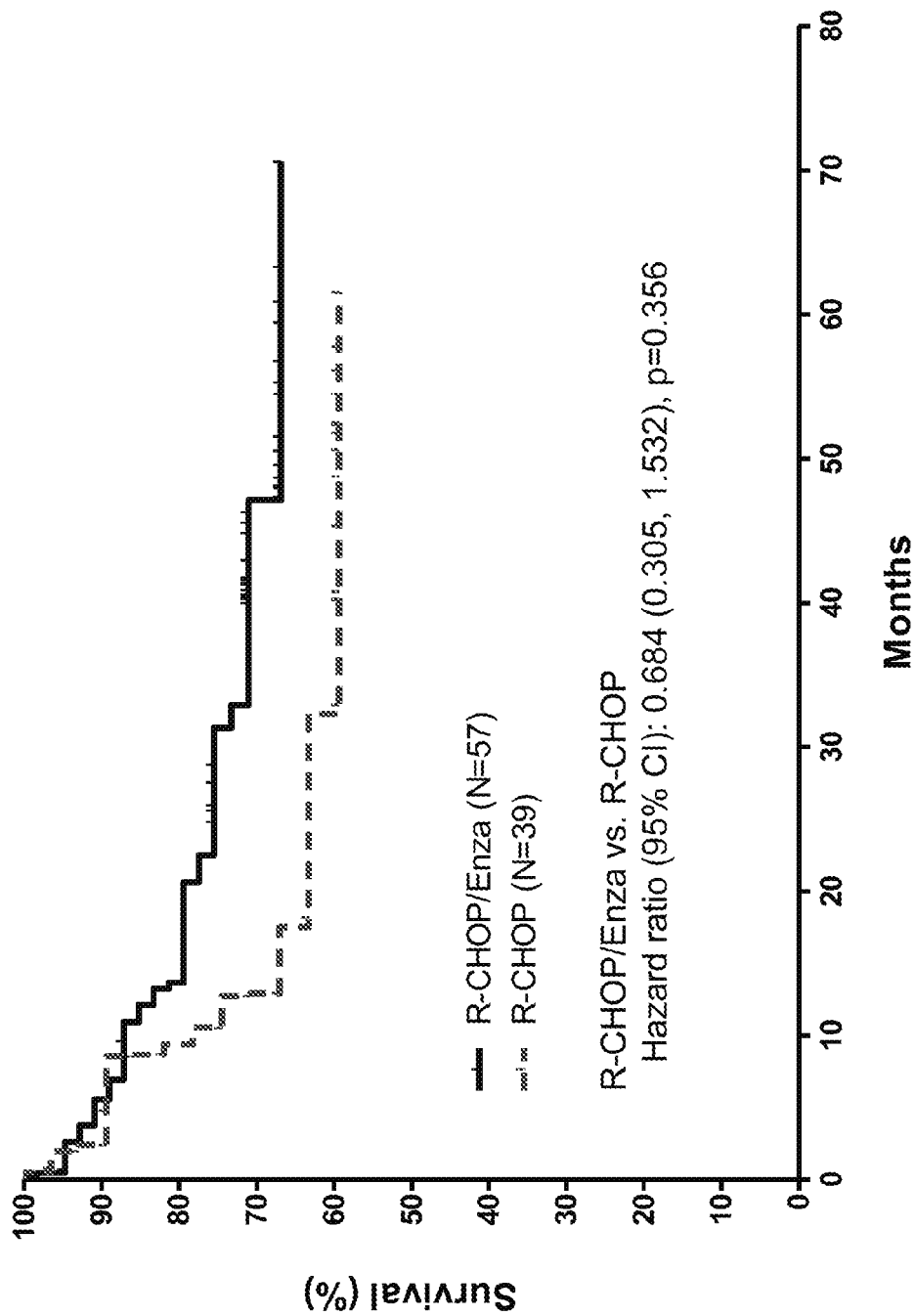

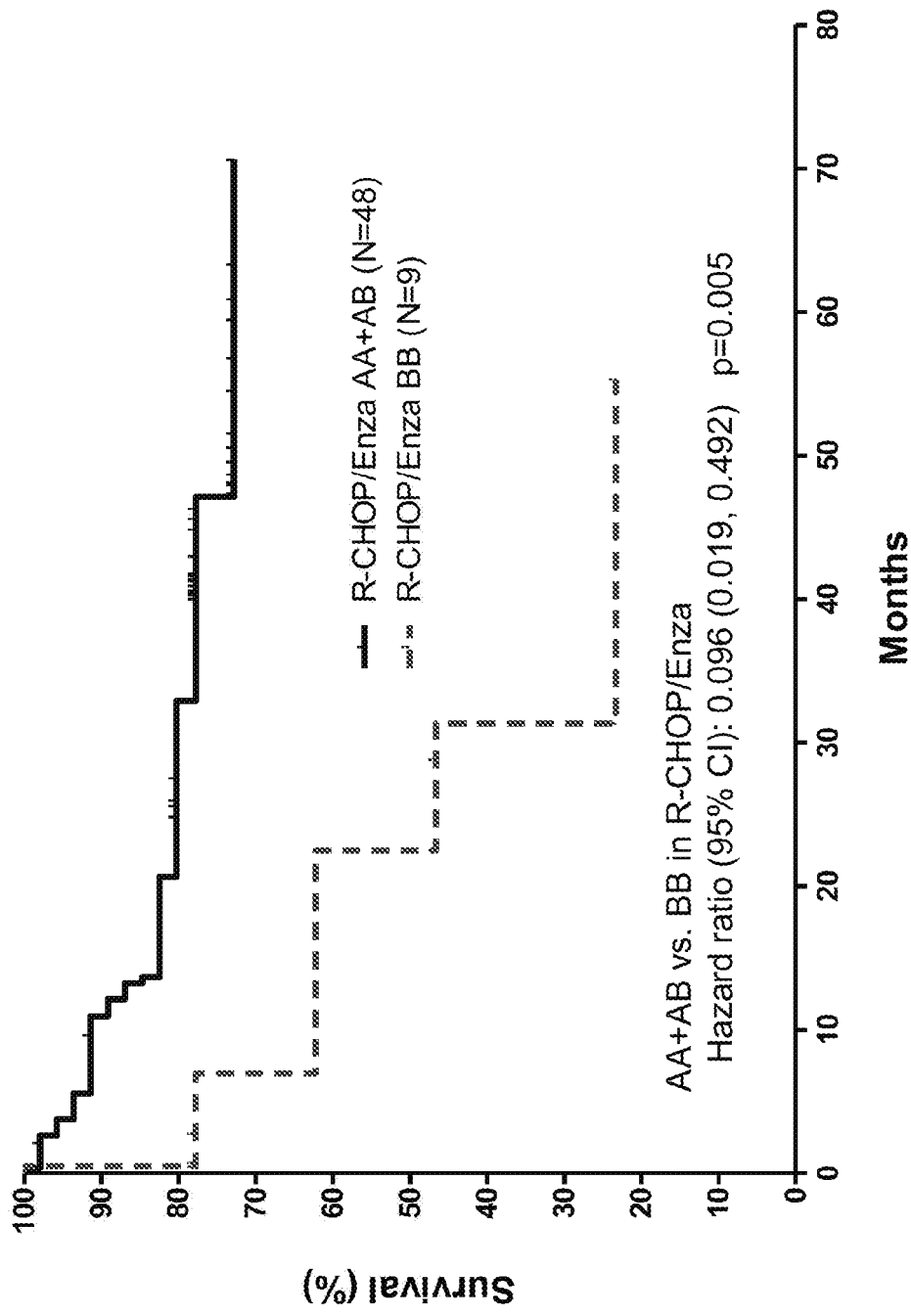

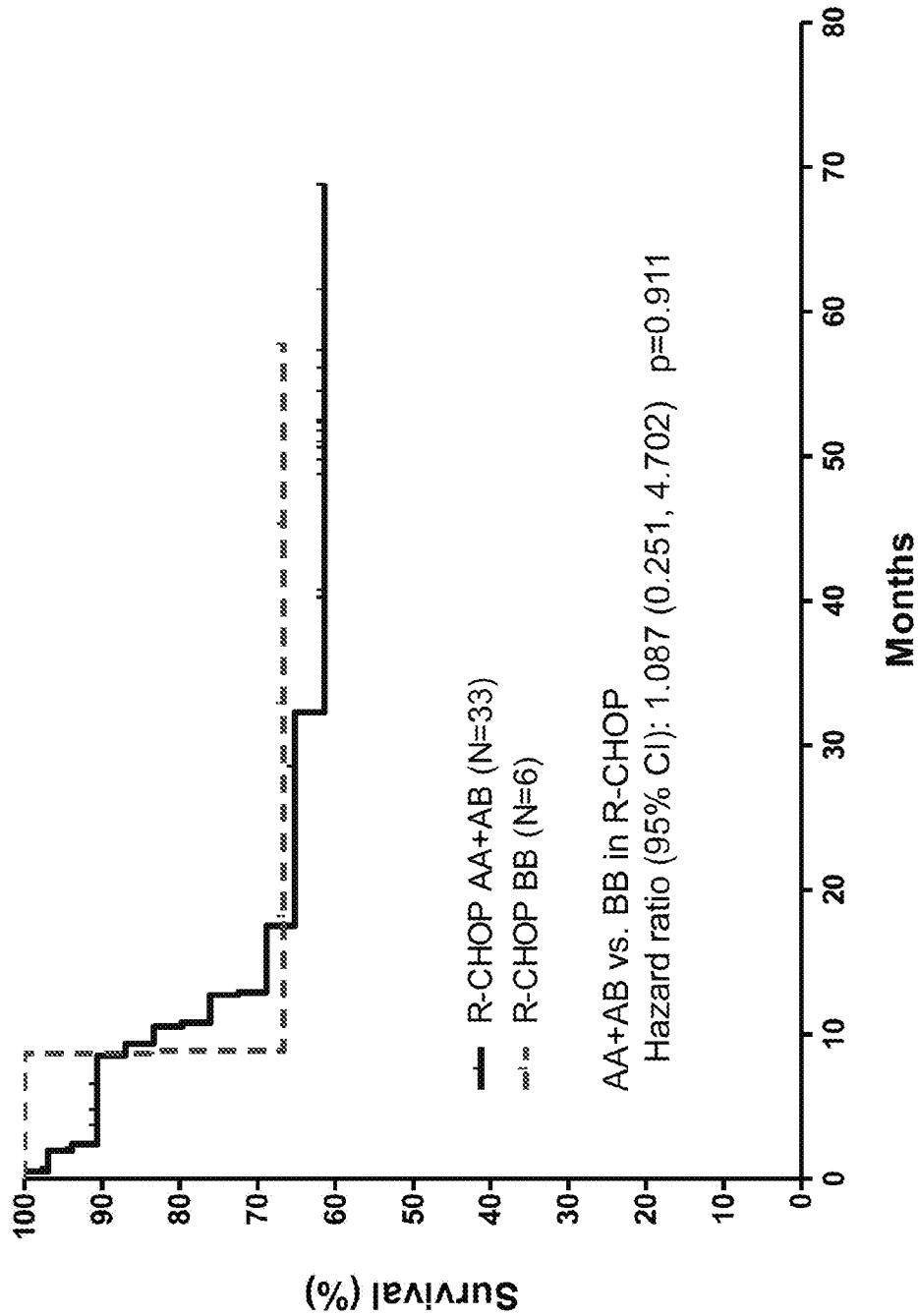
Figure 3D. S028 First Line Overall Survival in R-CHOP Treated Patients Carrying Different Genotypes

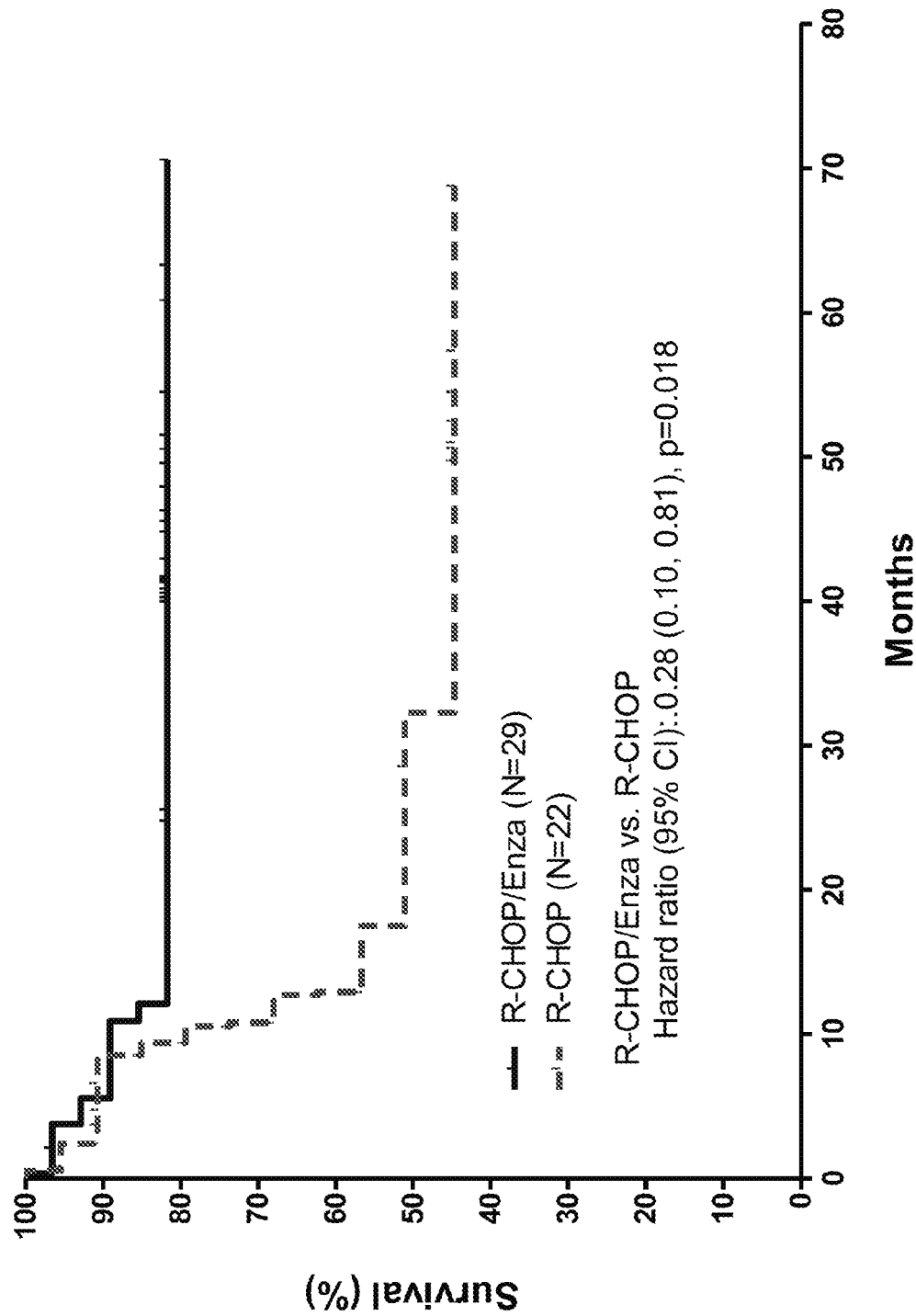
Figure 3E: Study S028 Kaplan-Meier Plot - Overall Survival In Patients IPI Score > 2 and Genotype AA+AB

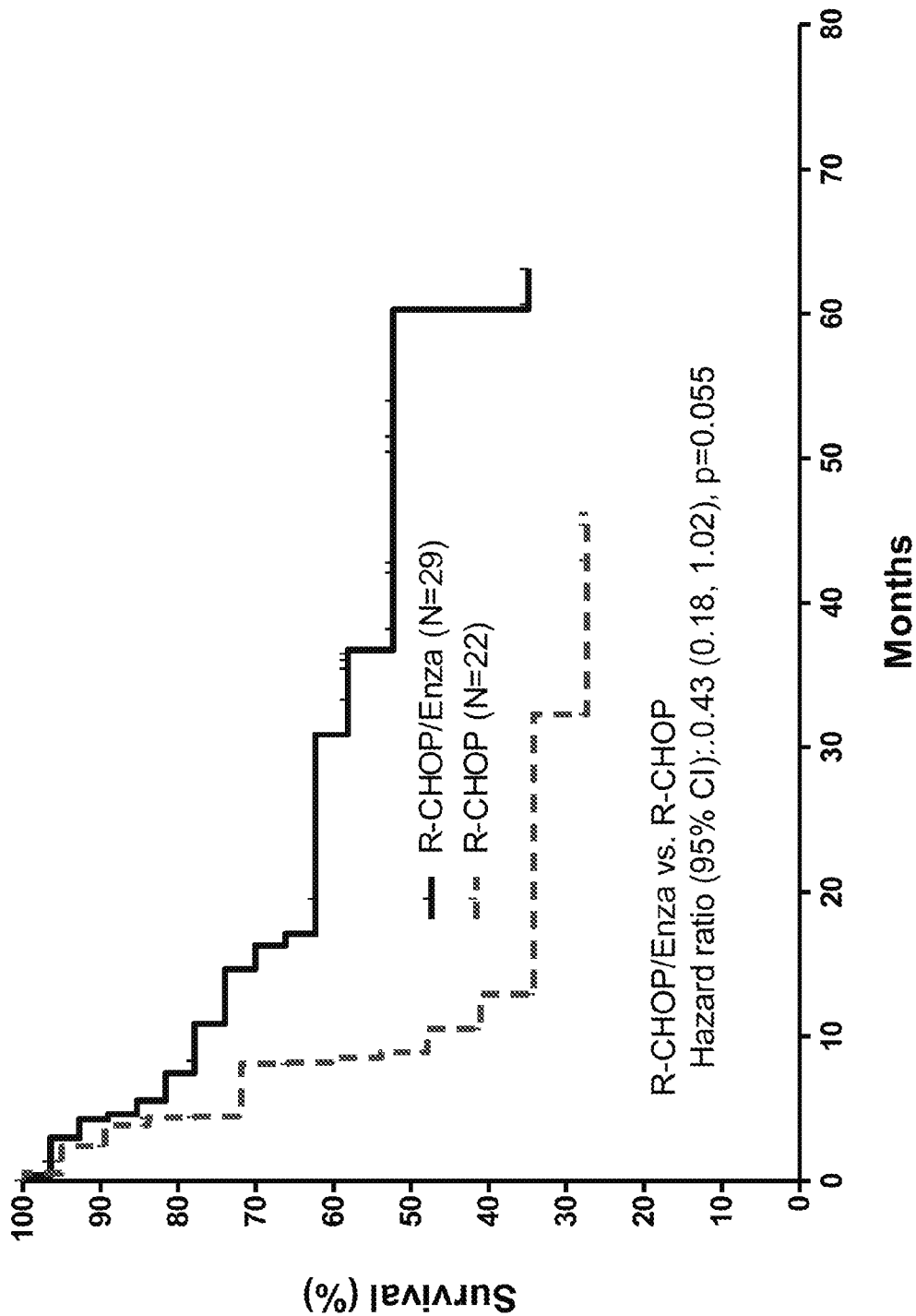

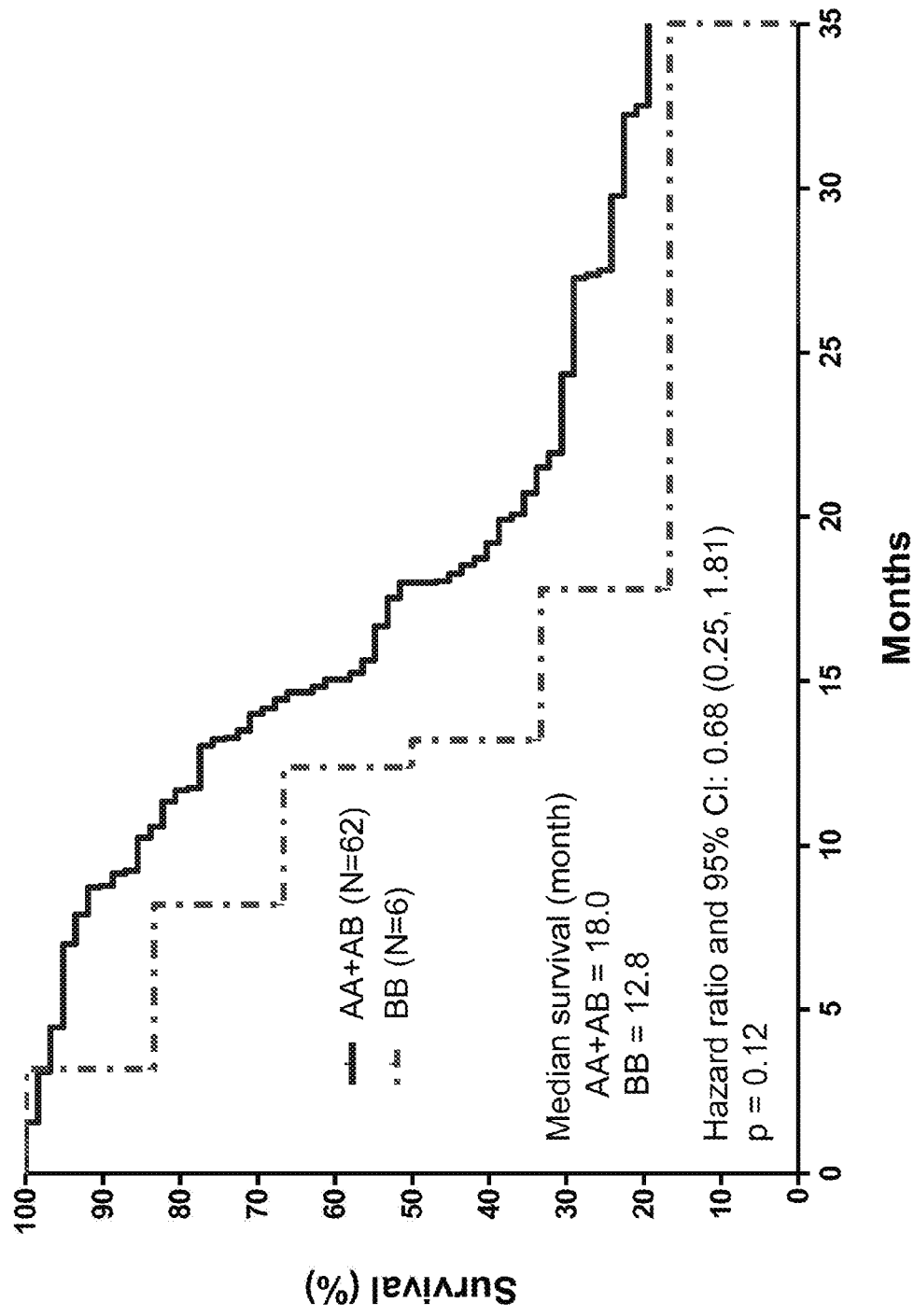

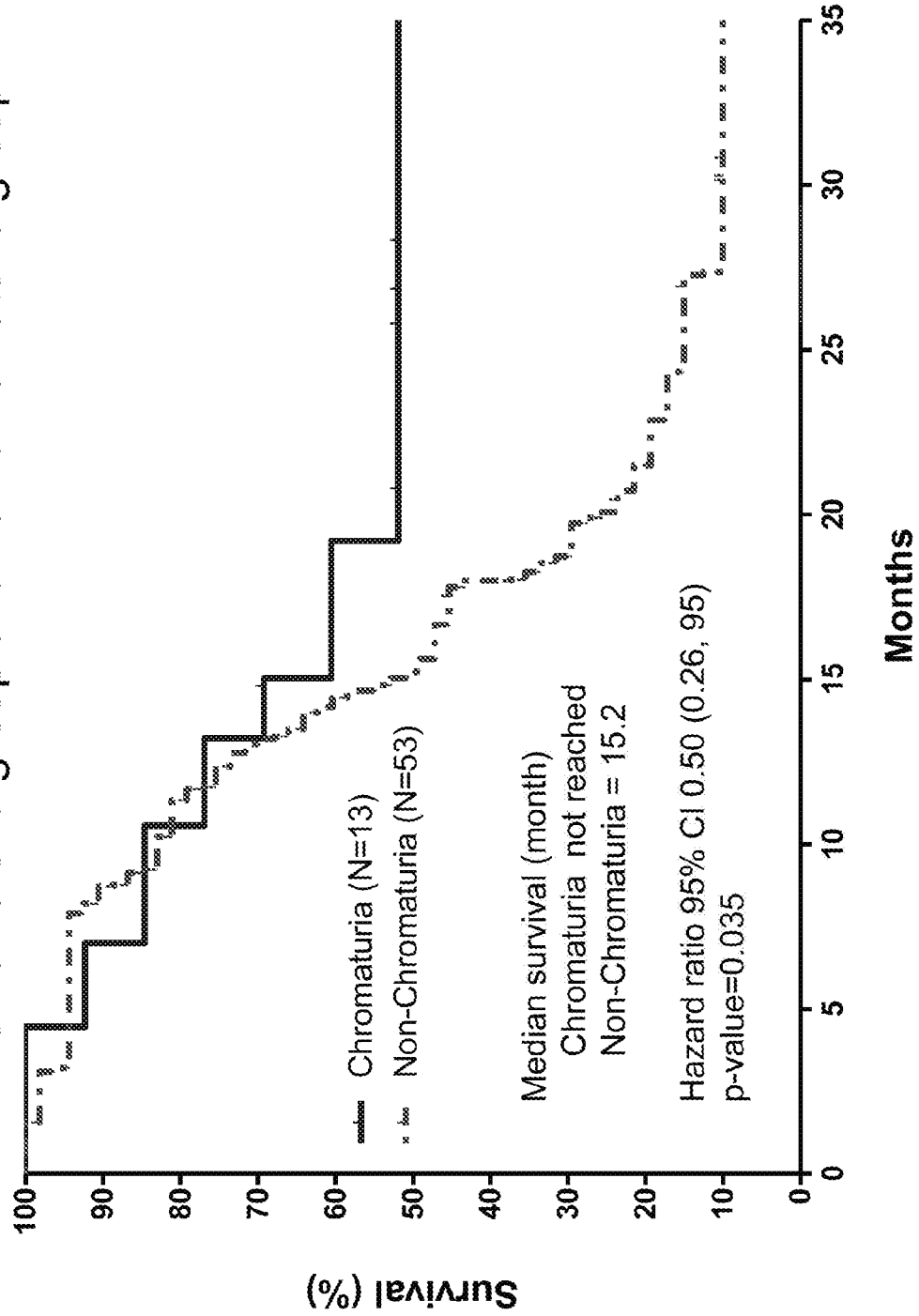

METHODS AND COMPOSITION FOR THE PREDICTION OF THE ACTIVITY OF ENZASTAURIN

CROSS-REFERENCE TO RELATED APPLICATIONS

This application is a U.S. national phase filing of International Patent Application Serial No. PCT/US2017/049747, entitled "METHODS AND COMPOSITION FOR THE PREDICTION OF THE ACTIVITY OF ENZASTAURIN," which claims priority to U.S. Provisional Application No. 62/382,734, entitled "Compositions and Methods Using a Pharmacogenomics Marker," filed 1 Sep. 2016, and U.S. Provisional Application No. 62/414,601, entitled "Compositions and Methods Using a Pharmacogenomics Marker," filed 28 Oct. 2016, the contents of the above applications are incorporated herein by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 669602000440SeqList.txt, date recorded: Aug. 30, 2017, size: 5,903 bytes).

TECHNICAL FIELD

The present invention relates to the field of pharmacogenomics, which applies one or more genomic biomarkers and the related diagnostic methods, devices, reagents, systems, and kits, for predicting varied individual responses such as, for example, efficacy or adverse effect, to therapeutic agents.

BACKGROUND

Pharmacogenomics is the study of inheritable traits affecting subject response to drug treatment. Differential responses to drug treatment may be due to underlying genetic polymorphisms (genetic variations sometimes called mutations) that affect drug metabolism. Testing subjects for these genetic polymorphisms may help to prevent adverse drug reactions and facilitate appropriate drug dosing regimens.

In the clinical setting, pharmacogenomics may enable physicians to select the appropriate pharmaceutical agents, and the appropriate dosage of these agents, for each individual subject. That is, pharmacogenomics can identify those subjects with the right genetic makeup to respond to a given therapy. In addition, pharmacogenomics can identify those subjects with genetic variations in the genes that control the metabolism of pharmaceutical compounds, so that the proper treatment (or no treatment) decision can be made, and the proper dosage can be administered.

Cancer is a disease with extensive heterogeneity. Although conventional histological and clinical features may correlate to cancer prognosis, the same apparent prognostic type of tumors varies widely in its responsiveness to therapy and consequent survival of the patient. New prognostic and predictive markers, which would facilitate an individualization of therapy for each patient, are needed to accurately predict patient response to treatments, such as small molecule or biological molecule drugs, in the clinic.

The problem may be solved by the identification of new parameters that could better predict the patient's sensitivity to treatment. The classification of patient samples is a crucial aspect of cancer diagnosis and treatment. The association of a patient's response to a treatment with molecular and genetic markers can open up new opportunities for treatment development in non-responding patients, or distinguish a treatment's indication among other treatment choices because of higher confidence in the efficacy. Further, the pre-selection of patients who are likely to respond well to a medicine, drug, or combination therapy may reduce the number of patients needed in a clinical study or accelerate the time needed to complete a clinical development program. The ability to determine which patients are responding to anti-angiogenesis therapies or predict drug sensitivity in patients is particularly challenging because drug responses reflect not only properties intrinsic to the target cells, but also a host's metabolic properties. Efforts to use genetic information to predict or monitor drug response have primarily focused on individual genes that have broad effects, such as the multidrug resistance genes mdrl and mrpl.

There is a need for new and alternative compositions and methods to determine drug sensitivity or monitor response in patients to allow the development of individualized treatment for diseases and disorders based on patient response at a molecular level. Pharmacogenomics may be used to discover and/or develop new and improved compositions and methods for cancer treatment and prognosis.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, the present disclosure describes one or more genomic biomarkers that correlate with different responses (e.g., efficacy, adverse effect, and other end points) among patients receiving a cancer treatment regime, such as enzastaurin, for treating diseases such as lymphoma, glioma/glioblastoma, and other cancers. The biomarker or biomarkers can be used in companion diagnostic tests which can help to predict drug responses and apply drugs only to those who will be benefited, and/or exclude those who might have negative outcome and/or adverse effects due to the treatment.

In one aspect, the present invention provides a panel of biomarkers comprising a single nucleotide polymorphisms (SNPs) selected from the group consisting of rs309605, rs309604, and other SNPs such as those from Tables 1A to 1H and Table 2, or complementary sequences thereof, and/or sequences in linkage disequilibrium therewith. In some embodiments, the biomarkers may comprise the nucleotide sequences set forth in SEQ ID NOs: 1-28, for example, SEQ ID NO: 1 and SEQ ID NO: 2, or complementary sequences thereof, and/or sequences in linkage disequilibrium therewith. In some embodiments, the biomarkers may also include chromaturia, which is also associated with enzastaurin efficacy.

In a further aspect, provided herein is a reagent for the assessment of the biomarkers disclosed herein, which may comprise one or more molecules for assaying the SNP. In some embodiments, the molecules may be oligonucleotides or polypeptides. In some embodiments, the oligonucleotides may comprise the nucleotide sequences set forth in SEQ ID NOs: 1-28, for example, SEQ ID NO: 1 and SEQ ID NO: 2, or complementary sequences thereof. In some embodiments, the SNP may be assayed by PCR, sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

In an additional aspect, provided herein is a kit for the assessment of a panel of isolated biomarkers, which comprises the reagent disclosed herein. In some embodiments, the biomarker or biomarkers comprise one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In some embodiments, the kit may further comprise instructions for using the biomarker to conduct a companion diagnostic test.

In yet another aspect, provided herein is a companion diagnostic test for a treatment. For example, the companion diagnostic test uses one or more markers selected from the group consisting of: rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary sequence thereof, and a sequence in linkage disequilibrium therewith. For example, the companion diagnostic test uses a panel of isolated biomarkers comprising one or more markers selected from the group consisting of: rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary sequence thereof, and a sequence in linkage disequilibrium therewith. In some embodiments, the companion diagnostic test may comprise: a) obtaining a biological sample from a subject that is undergoing a treatment or is considered for a treatment; b) isolating genomic DNA from said biological sample; c) assaying the panel of biomarkers; d) generating an output with a computer algorithm based on the assay results of said panel of biomarkers; and/or e) determining the likely responsiveness of said subject to said treatment. In some embodiments, the SNPs may be assayed by PCR, sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

In one aspect, disclosed herein is a panel of isolated biomarkers associated and/or linked with two, three, four or more of the SNPs disclosed herein, for example, rs309605 and those in Tables 1A to 1H and Table 2. In another aspect, disclosed herein is a companion diagnostic test for a treatment using one or more isolated biomarkers associated and/or linked with one, two, three, four or more of the SNPs disclosed herein, for example, rs309605 and those in Tables 1A to 1H and Table 2.

Further provided is a method of prognosticating responsiveness of a subject to a disease treatment using the companion diagnostic test disclosed herein. In some embodiments, the treatment may comprise a therapeutic regimen using enzastaurin or other PKC-β inhibitors. In some embodiments, the disease is selected from the group consisting of DLBCL, glioblastoma, lung cancer, prostate cancer, and breast cancer. In some embodiments, the method is used for selecting a patient who is likely to benefit from the treatment and/or excluding a patient who is likely to experience an adverse effect from the treatment.

In still another aspect, provided herein is a method of identifying a new biomarker using the panel of isolated biomarkers disclosed herein. In some embodiments, the new biomarker may be a DNA, a RNA, a polypeptide, a siRNA or another form of biomarker. Further provided herein is a method of identifying a drug target using the panel of isolated biomarkers disclosed herein. In some embodiments, the drug target may be identified based on a biological pathway related to a biomarker, wherein the biological pathway may be selected from the genes related to or regulated by the genomic regions affected by the SNP(s) disclosed herein, such as rs309605 or rs309604.

In one aspect, disclosed herein is an isolated polynucleotide comprising, consisting of, or consisting essentially of a single nucleotide polymorphism (SNP) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In one embodiment, in the isolated polynucleotide of the present disclosure, the SNP is rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, or rs309601. In another embodiment, the SNP is rs309605, rs309604, rs5894240, rs1494748, rs7836309, rs309607, rs2132025, rs11990158, rs6469570, rs309603, rs923967, rs309606, rs72675965, rs309602, rs309608, rs309610, rs2575911, rs309609, or rs309601. In yet another embodiment, the SNP is rs309605, rs309604, rs5894240, rs1494748, or rs7836309. In one embodiment, the SNP is rs309605 or rs309604.

In another aspect, disclosed herein is a panel of isolated polynucleotides comprising, consisting of, or consisting essentially of two or more, three or more, four or more, or five or more of the isolated polynucleotide of any one of the preceding embodiments. In one embodiment, the SNPs comprise two or more, three or more, four or more, five or more, or all of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, and rs309601. In another embodiment, the SNPs comprise two or more, three or more, four or more, five or more, or all of rs309605, rs309604, rs5894240, rs1494748, rs7836309, rs309607, rs2132025, rs11990158, rs6469570, rs309603, rs923967, rs72675965, rs309602, rs309608, rs309610, rs2575911, rs309609, and rs309601. In yet another embodiment, the SNPs comprise two or more, three or more, four or more, or all of rs309605, rs309604, rs5894240, rs1494748, and rs7836309. In one embodiment, the SNPs comprise rs309605 and/or rs309604.

In any of the preceding embodiments, the isolated polynucleotide can comprise, consist of, or consist essentially of a sequence set forth in SEQ ID NOs: 1-28, a complementary sequence thereof, or a sequence in linkage disequilibrium therewith. In one embodiment, the isolated polynucleotide comprises, consists of, or consists essentially of a sequence set forth in SEQ ID NOs: 1-11, 15-21, and 28, a complementary sequence thereof, or a sequence in linkage disequilibrium therewith. In one embodiment, the isolated polynucleotide comprises, consists of, or consists essentially of a sequence set forth in SEQ ID NOs: 1-5, a complementary sequence thereof, or a sequence in linkage disequilibrium therewith. In another embodiment, the isolated polynucleotide comprises, consists of, or consists essentially of a sequence set forth in SEQ ID NOs: 1-2, a complementary sequence thereof, or a sequence in linkage disequilibrium therewith.

In one aspect, disclosed herein is a kit comprising the isolated polynucleotide or panel of any one of the preceding embodiments, which kit optionally comprises an instruction for use.

In another aspect, provided herein is a microarray comprising a substrate and the isolated polynucleotide or panel of any one of the preceding embodiments directly or indirectly immobilized on the substrate.

In yet another aspect, disclosed herein is a reagent for detecting one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In one embodiment, the reagent is for detecting one or more SNPs selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, and rs309601. In one embodiment, the reagent is for detecting one or more SNPs selected from the group consisting of rs309605, rs309604, rs5894240, rs1494748, rs7836309, rs309607, rs2132025, rs11990158, rs6469570, rs309603, rs923967, rs309606, rs72675965, rs309602, rs309608, rs309610, rs2575911, rs309609, and rs309601. In one embodiment, the reagent is for detecting one or more SNPs selected from the group consisting of rs309605, rs309604, rs5894240, rs1494748, and rs7836309. In one embodiment, the reagent is for detecting rs309605 and/or rs309604.

In any of the preceding embodiments, the SNP or SNPs can comprise a sequence set forth in SEQ ID NOs: 1-28, a complementary sequence thereof, or a sequence in linkage disequilibrium therewith. In one embodiment, the SNP or SNPs comprise a sequence set forth in SEQ ID NOs: 1-11, 15-21, and 28, a complementary sequence thereof, or a sequence in linkage disequilibrium therewith. In another embodiment, the SNP or SNPs comprise a sequence set forth in SEQ ID NOs: 1-5, a complementary sequence thereof, or a sequence in linkage disequilibrium therewith. In another embodiment, the SNP or SNPs comprise a sequence set forth in SEQ ID NOs: 1-2, a complementary sequence thereof, or a sequence in linkage disequilibrium therewith.

In any of the preceding embodiments, the reagent can comprise one or more molecules for assaying the SNP or SNPs. In one embodiment, the one or more molecules comprise an oligonucleotide and/or a polypeptide. In one embodiment, the oligonucleotide comprises a sequence set forth in SEQ ID NOs: 1-28, or a complementary sequence thereof. In any of the preceding embodiments, the oligonucleotide can comprise one or more primers for genotyping the SNP or SNPs.

In one aspect, disclosed herein is a kit comprising the reagent of any of the preceding embodiments, which kit optionally comprises an instruction for use. In another aspect, disclosed herein is a kit comprising the isolated polynucleotide or panel of any of the preceding embodiments, which kit optionally comprises an instruction for use. In one embodiment, the isolated polynucleotide or panel comprises a SNP selected from the group consisting of rs309605, rs309604, rs5894240, rs1494748, rs7836309, rs309607, rs2132025, rs11990158, rs6469570, rs309603, rs923967, rs309606, rs72675965, rs309602, rs309608, rs309610, rs2575911, rs309609, and rs309601, and the reagent is capable of detecting the SNP(s). In another embodiment, the panel comprises rs309605, rs309604, rs5894240, rs1494748, and/or rs7836309, and the reagent is capable of detecting the SNPs. In one embodiment, the panel comprises rs309605 and/or rs309604, and the reagent is capable of detecting the SNPs.

In any of the preceding kit embodiments, the reagent can be capable of detecting the SNP(s), and the isolated polynucleotide or panel can serve as a control for a detection assay.

In one aspect, disclosed herein is a microarray comprising a substrate and the reagent of any one of the preceding embodiments directly or indirectly immobilized on the substrate. In another aspect, disclosed herein is a microarray comprising a substrate and the isolated polynucleotide, panel, or reagent of any one of the preceding embodiments directly or indirectly immobilized on the substrate. In one embodiment, the reagent is capable of detecting the SNP(s) and the isolated polynucleotide or panel serves as a control for a detection assay.

In any of the preceding embodiments, the kit, reagent, or microarray can be used for the assessment of an isolated biomarker or a panel of isolated biomarkers. In particular embodiments, the biomarker or biomarkers comprise a SNP selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In one embodiment, the isolated biomarker or panel is assayed by sequencing, polymerase chain reaction (PCR), capillary electrophoresis, mass spectrometry, single-strand conformation polymorphism (SSCP), electrochemical analysis, denaturing HPLC and gel electrophoresis, restriction fragment length polymorphism, hybridization analysis, single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), loop-mediated isothermal amplification (LAMP), hybridization, nucleic acid sequencing, and/or microarray. Optionally, the nucleic acid sequencing is selected from the group consisting of Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunneling currents DNA sequencing, sequencing by hybridization, sequencing with mass spectrometry, microfluidic Sanger sequencing, a microscopy-based technique, RNAP sequencing, and in vitro virus high-throughput sequencing.

In any of the preceding embodiments, the kit, reagent, or microarray can further comprise an instruction for using the isolated biomarker or panel to conduct a companion diagnostic test for a treatment, e.g., a cancer treatment. In one aspect, the companion diagnostic test for the treatment is conducted using a panel of isolated biomarkers comprising one or more SNPs selected from the group consisting of rs309605, rs309604, rs5894240, rs1494748, rs7836309, rs309607, rs2132025, rs11990158, rs6469570, rs309603, rs923967, rs309606, rs72675965, rs309602, rs309608, rs309610, rs2575911, rs309609, rs309601, a complementary SNP thereof, and a SNP in linkage disequilibrium therewith. In one embodiment, the companion diagnostic test for the treatment is conducted using a panel of isolated biomarkers comprising one or more SNPs selected from the group consisting of rs309605, rs309604, rs5894240, rs1494748, rs7836309, a complementary SNP thereof, and a SNP in linkage disequilibrium therewith. In another aspect, the companion diagnostic test for the treatment is conducted using a panel of isolated biomarkers comprising one or more SNPs selected from the group consisting of rs309605, rs309604, a complementary SNP thereof, and a SNP in linkage disequilibrium therewith.

In any of the preceding embodiments, the treatment can be a cancer treatment. In some embodiments, the cancer is a lymphoma, a leukemia, a brain cancer, a multiple myeloma, a pancreatic cancer, a liver cancer, a stomach cancer, a breast cancer, a kidney cancer, a lung cancer, a colorectal cancer, a colon cancer, a prostate cancer, an ovarian cancer, a cervical cancer, a skin cancer, an esophagus cancer, or a head and neck cancer. In some embodiments, the cancer is diffuse large B-cell lymphoma (DLBCL), glioma/glioblastoma (GBM), non-small cell lung cancer (NSCLC), breast cancer, prostate cancer, ovarian cancer, colon cancer, pancreatic cancer, renal cancer, and other hematology tumors such as cutaneous T-cell lymphomachronic lymphocytic leukemia, multiple myeloma, or a non-Hodgkin lymphoma, such as Waldenstrom's macroglobulinemia.

In any of the preceding embodiments, the treatment can comprise administering to a subject in need thereof a pharmaceutically effective amount of a bisindolylmaleimide or an analogue or derivative thereof. In one embodiment, the bisindolylmaleimide or analogue or derivative is enzastaurin or an analogue or derivative thereof.

In any of the preceding embodiments, the treatment can comprise administering to a subject in need thereof a pharmaceutically effective amount of a protein kinase inhibitor, such as a protein kinase C (PKC) inhibitor, e.g., a PKCβ inhibitor. In one embodiment, the protein kinase inhibitor is enzastaurin or an analogue or derivative thereof.

In any of the preceding embodiments, the protein kinase inhibitor can suppress phosphorylation of AKT, mammalian target of rapamycin (mTOR), p70S6K, ribosomal protein S6, 4EBP1, cAMP response element-binding protein, and/or GSK3β, and/or the protein kinase inhibitor can inhibit or reduce the response of an endothelial cell to an angiogenic stimulus, e.g., VEGF.

In any of the preceding embodiments, the kit, reagent, or microarray can further comprise a bisindolylmaleimide or an analogue or derivative thereof, and/or a protein kinase inhibitor, such as a protein kinase C (PKC) inhibitor, e.g., a PKCβ inhibitor. In one embodiment, the bisindolylmaleimide or analogue or derivative and/or the protein kinase inhibitor is enzastaurin or an analogue or derivative thereof.

In one aspect, disclosed herein is a companion diagnostic method, comprising:

a) obtaining a biological sample from a subject that is undergoing a treatment or is considered for a treatment, and optionally isolating genomic DNA from said biological sample;

b) assaying the biological sample for one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith; and/or c) generating an output, e.g., a score, for example with a computer algorithm based on the assay results of said SNP or SNPs, in order to determine the likely responsiveness of said subject to said treatment.

In one aspect, disclosed herein is a method for classifying a subject for eligibility for a treatment, comprising:

a) obtaining a biological sample from a subject that is undergoing a treatment or is considered for a treatment, and optionally isolating genomic DNA from said biological sample;

b) assaying the biological sample for one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith; and/or c) generating an output, e.g., a score, for example with a computer algorithm based on the assay results of said SNP or SNPs, in order to classify the subject as eligible or ineligible for the treatment or continued treatment.

In one aspect, disclosed herein is a method for screening a subject or a population of subjects for a treatment, comprising:

a) obtaining a biological sample from a subject or a population of subjects undergoing a treatment or being considered for a treatment, and optionally isolating genomic DNA from said biological sample;

b) assaying the biological sample for one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith; and/or c) generating an output, e.g., a score, for example with a computer algorithm based on the assay results of said SNP or SNPs, in order to determine whether the subject or the population is likely to benefit from the treatment or continued treatment, and/or to determine whether the subject or the population is likely to experience an adverse effect from the treatment or continued treatment.

In one aspect, disclosed herein is a method for monitoring a subject during a treatment, comprising:

a) obtaining a biological sample from a subject undergoing a treatment, and optionally isolating genomic DNA from said biological sample;

b) assaying the biological sample for one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith; and/or c) generating an output, e.g., a score, for example with a computer algorithm based on the assay results of said SNP or SNPs, in order to determine whether the subject should receive continued treatment.

In any of the preceding embodiments, the method can further comprise obtaining information of the subject's chromaturia status before, during, and/or after the treatment. In one embodiment, the information of the subject's chromaturia status is obtained from the subject's medical record, and/or obtained by self-reporting and/or analysis of a urine sample of the subject during the treatment.

In any of the preceding embodiments, the SNP(s) assay output and the information of the subject's chromaturia status can be both used in guiding treatment decision-making Optionally, the output and the information produce a synergistic effect.

In any of the preceding embodiments, the method can further comprise subjecting the subject to the treatment or continuing the treatment on the subject.

In any of the preceding embodiments, the method can further comprise not recommending the treatment on the subject or withdrawing the subject from the treatment.

In any of the preceding method embodiments, the one or more SNPs can be selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, and rs309601. In one embodiment, the one or more SNPs are selected from the group consisting of rs309605, rs309604, rs5894240, rs1494748, rs7836309, rs309607, rs2132025, rs11990158, rs6469570, rs309603, rs923967, rs72675965, rs309602, rs309608, rs309610, rs2575911, rs309609, and rs309601. In one aspect, the one or more SNPs are selected from the group consisting of rs309605, rs309604, rs5894240, rs1494748, or rs7836309. In another aspect, the one or more SNPs are selected from the group consisting of rs309605 and rs309604.

In any of the preceding method embodiments, the SNP or SNPs can comprise a sequence set forth in SEQ ID NOs: 1-28, a complementary sequence thereof, or a sequence in linkage disequilibrium therewith. In one aspect, the SNP or SNPs comprise a sequence set forth in SEQ ID NOs: 1-11, 15-21, and 28, a complementary sequence thereof, or a sequence in linkage disequilibrium therewith. In another aspect, the SNP or SNPs comprise a sequence set forth in SEQ ID NOs: 1-5, a complementary sequence thereof, or a sequence in linkage disequilibrium therewith. In still another aspect, the SNP or SNPs comprise a sequence set forth in SEQ ID NOs: 1-2, a complementary sequence thereof, or a sequence in linkage disequilibrium therewith.

In any of the preceding method embodiments, the SNP is or the SNPs can be assayed by sequencing, polymerase chain reaction (PCR), capillary electrophoresis, mass spectrometry, single-strand conformation polymorphism (SSCP), electrochemical analysis, denaturing HPLC and gel electrophoresis, restriction fragment length polymorphism, hybridization analysis, single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), loop-mediated isothermal amplification (LAMP), hybridization, nucleic acid sequencing, and/or microarray. Optionally, the nucleic acid sequencing can be selected from the group consisting of Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunneling currents DNA sequencing, sequencing by hybridization, sequencing with mass spectrometry, microfluidic Sanger sequencing, a microscopy-based technique, RNAP sequencing, and in vitro virus high-throughput sequencing.

In any of the preceding embodiments, the treatment can be a cancer treatment. In one aspect, the cancer is a lymphoma, a leukemia, a brain cancer, a multiple myeloma, a pancreatic cancer, a liver cancer, a stomach cancer, a breast cancer, a kidney cancer, a lung cancer, a colorectal cancer, a colon cancer, a prostate cancer, an ovarian cancer, a cervical cancer, a skin cancer, an esophagus cancer, or a head and neck cancer. In some embodiments, the cancer is diffuse large B-cell lymphoma (DLBCL), glioma/glioblastoma (GBM), non-small cell lung cancer (NSCLC), cutaneous T-cell lymphoma, or a non-Hodgkin lymphoma, such as Waldenstrom's macroglobulinemia.

In any of the preceding method embodiments, the treatment can comprise administering to the subject in need thereof a pharmaceutically effective amount of a bisindolylmaleimide or an analogue or derivative thereof. Optionally, the treatment can further comprise another therapy, such as a standard care for a disease or condition, e.g., rituximab-cyclophosphamide, doxorubicin, vincristine, and/or prednisone (R-CHOP) for cancer treatment. In one aspect, the bisindolylmaleimide or analogue or derivative is enzastaurin or an analogue or derivative thereof.

In any of the preceding embodiments, the treatment can comprise administering to the subject in need thereof a pharmaceutically effective amount of a protein kinase inhibitor, such as a protein kinase C (PKC) inhibitor, e.g., a PKCβ inhibitor. Optionally, the treatment can further comprise another therapy, such as a standard care for the disease or condition. In one embodiment, the protein kinase inhibitor is enzastaurin or an analogue or derivative thereof. In any of the preceding embodiments, the protein kinase inhibitor can suppress phosphorylation of AKT, mammalian target of rapamycin (mTOR), p70S6K, ribosomal protein S6, 4EBP1, cAMP response element-binding protein, and/or GSK3β. In any of the preceding embodiments, the protein kinase inhibitor can inhibit or reduce the response of an endothelial cell to an angiogenic stimulus, e.g., VEGF.

In one aspect, also disclosed herein is a method of identifying a new biomarker using one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In one embodiment, the new biomarker is a DNA, a RNA, a polypeptide, a siRNA or another form of biomarker.

Also disclosed herein, in one aspect, is a method of identifying a drug target using one or more single nucleotide polymorphisms (SNPs) selected from the group consisting of rs309605, rs309604, rs5894240, rs1494748, rs7836309, rs309607, rs2132025, rs11990158, rs6469570, rs309603, rs923967, rs1494751, rs2575943, rs167446, rs309606, rs72675965, rs309602, rs309608, rs309610, rs2575911, rs309609, rs170132, rs386413735, rs2642789, rs2642788, rs2575944, rs309614, rs309601, a complementary SNP thereof, and a SNP in linkage disequilibrium therewith. In one embodiment, the drug target is identified based on a biological pathway related to the one or more SNPs.

BRIEF DESCRIPTION OF THE DRAWINGS

FIGS. 1A-1C. FIG. 1A depicts the enzastaurin phase 3 Prelude trial design. Enzastaurin's anti-tumor activity in DLBCL was examined in a phase 3 maintenance trial (Prelude) where 758 patients were randomized in 2:1 ratio in enzastaurin treatment arm vs placebo control arm. FIG. 1B shows the correlation of chromaturia with enzastaurin efficacy. Overall survival analysis of patients treated with enzastaurin (N=504) vs patients treating with placebo control arm (N=254) was shown and there is no significant difference between enzastaurin arm and placebo arm. FIG. 1C shows the survival analysis of patients experiencing chromaturia (N=96) vs patient without chromaturia (N=408) following enzastaurin treatment, and also vs. the control arm (N=254). By this analysis, the patients experiencing chromaturia after Enzastaurin treatment exhibiting significantly longer overall survival than that of the control group (Hazard Ratio=0.46 and p-value=0.025).

The Kaplan-Meier estimate, also known as the product limit estimate, is a non-parametric statistic used to estimate the survival function from lifetime data. Plot based on such estimate method is called Kaplan-Meier plot. Kaplan-Meier technique is widely used in medical and clinical research to analyze time to event variables, such overall survival and disease-free survival. These time to event variables often do not satisfy an underline specific survival function, such as exponential or Weibull distribution. Therefore, Kaplan-Meier technique provides a practical and least-bias estimate of survival function for common time to event variables.

FIGS. 2A-2C show the prediction of enzastaurin efficacy by the genetic biomarker rs309605. FIG. 2A depicts the overall survival analysis of patients from the enzastaurin arm. The survival curves show patients carrying rs309605 genotype AA and AB vs patients carrying genotype BB. FIG. 2B shows the overall survival analysis of patients from the placebo arm. The survival curves show patients carrying rs309605 genotype AA and AB vs patients carrying genotype BB. FIG. 2C shows the result of predicting enzastaurin efficacy by combining rs309605 and chromaturia.

Figure 3A:
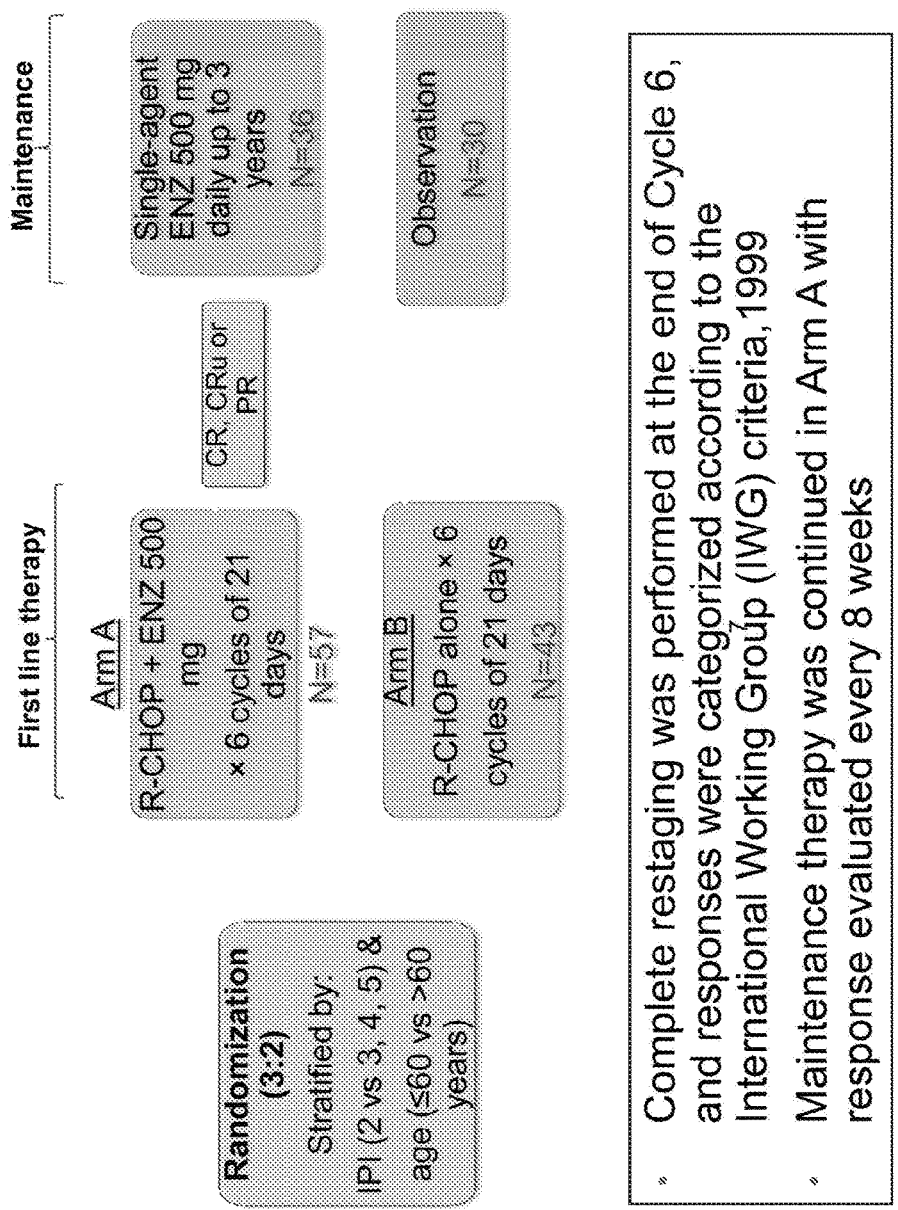

FIGS. 3A-3F show the biomarker analysis in enzastaurin Phase 2 DLBCL 1$^{st}$ line induction trial. FIG. 3A shows the phase 2 DLBCL Trial design. FIG. 3B shows the overall survival analysis in general patient population. FIG. 3C shows the survival analysis in patients carrying different rs309605 genotypes. FIG. 3D shows the biomarker analysis in placebo group. FIG. 3E shows a Kaplan-Meier plot of Study S028, showing the overall survival in patients with International Prognostic Index (IPI) Score>2 and Genotype AA+AB. FIG. 3F shows a Kaplan-Meier plot of Study S028, showing the Progression Free Survival (PFS) in patients with IPI Score>2 and Genotype AA+AB.

FIGS. 4A-4B show the biomarker analysis in enzastaurin in GBM Phase ½ first line trial. FIG. 4A is a Kaplan-Meier plot showing time to overall survival in the AA+AB group and BB group. FIG. 4B is a Kaplan-Meier plot showing time to overall survival in the chromaturia group and non-chromaturia group.

Figure 5A:
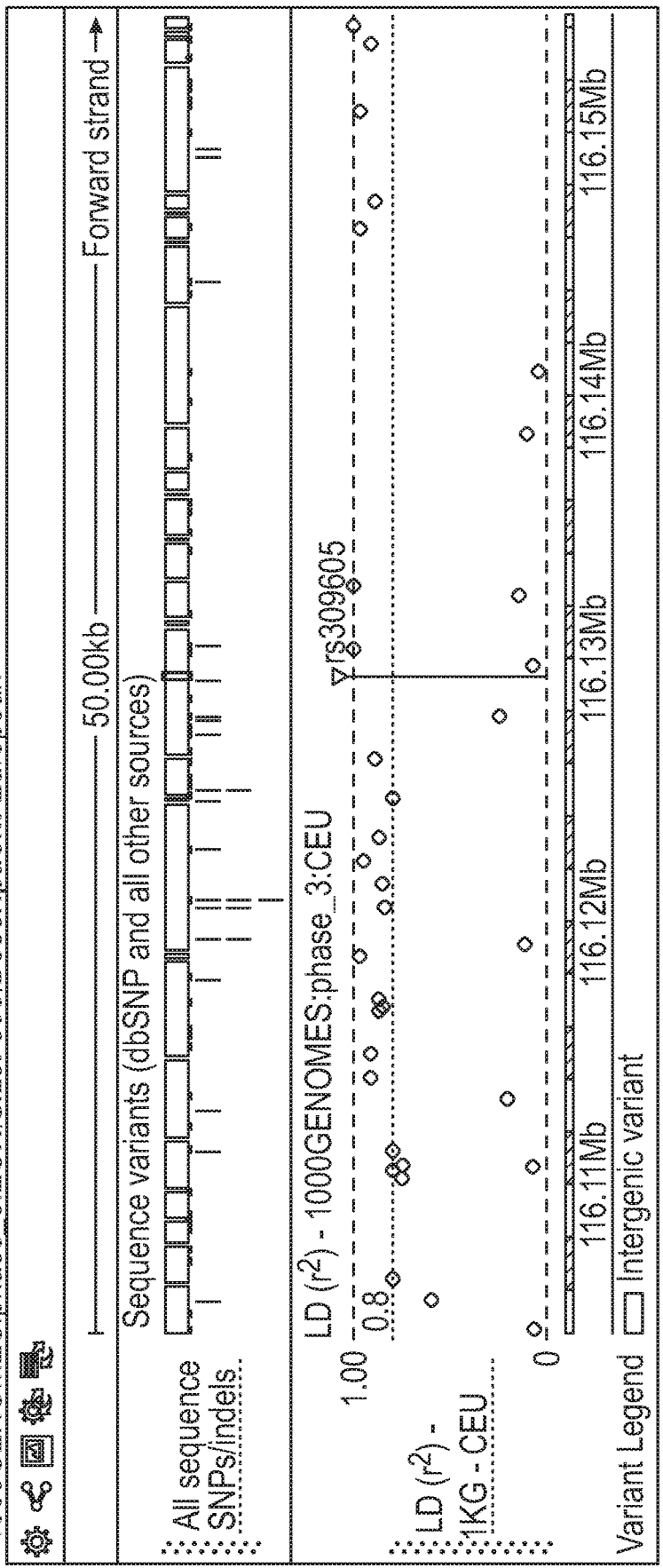
Figure 5B:
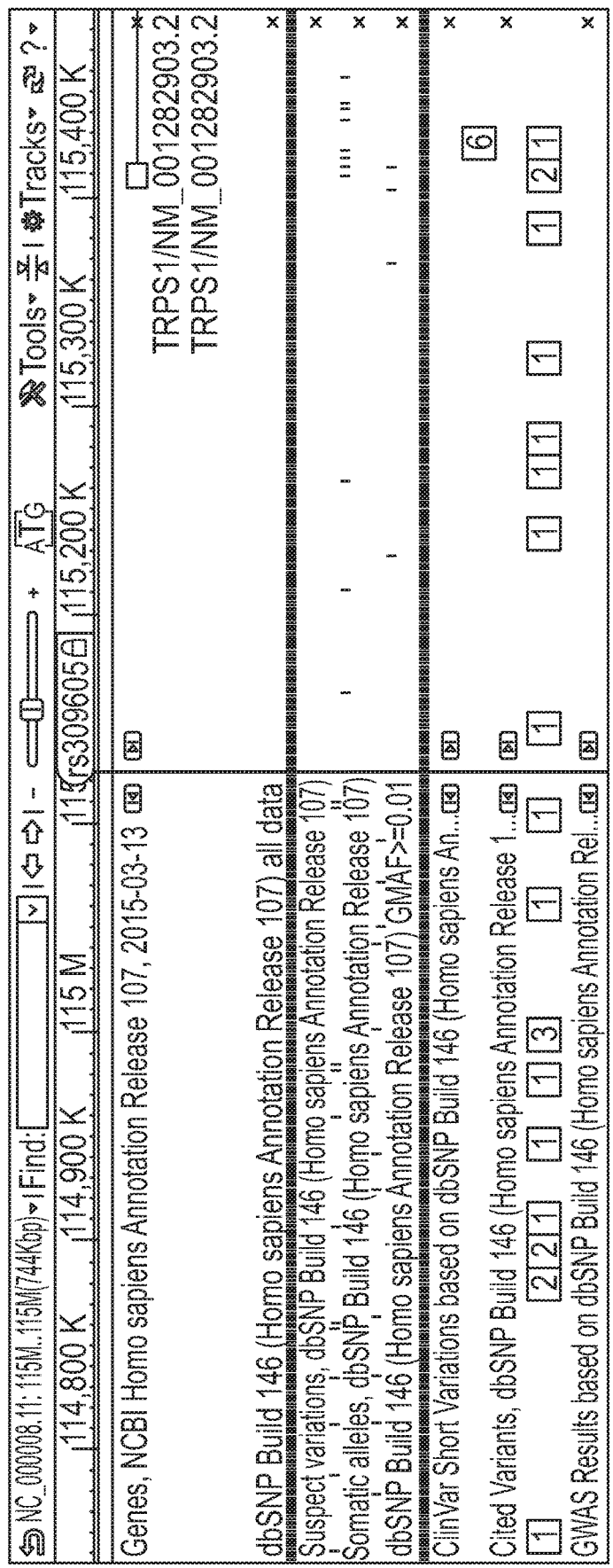

FIGS. 5A-5B. FIG. 5A shows a linkage disequilibrium map around rs309605. In this example, the Linkage Disequilibrium of rs309605 is for CEU. The result is from 1000 GENOMES phase 3 data. CEU represents Utah residents with Northern and Western European ancestry. FIG. 5B shows a detailed analysis of rs309605 and TRPS1 gene, indicating the physical location of rs309605 on Chr8 and its closest gene TRPS1.

DETAILED DESCRIPTION OF THE INVENTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patients, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimens.

As used herein, a "pharmacogenomic biomarker" is an objective biomarker which correlates with a specific clinical drug response or susceptibility in a subject (see, e.g., McLeod et al., Eur. J. Cancer (1999) 35:1650-1652). It may be a biochemical biomarker, or a clinical sign or symptom. The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of DNA, RNA, or protein for specific tumor markers in a subject, a drug or course of treatment may be selected that is optimized for the treatment of the specific tumor likely to be present in the subject. Similarly, the presence or absence of a specific sequence mutation or polymorphism may correlate with drug response. The use of pharmacogenomic biomarkers therefore permits the application of the most appropriate treatment for each subject without having to administer the therapy. Methods for discovering pharmacogenomic biomarkers are known, for example, as disclosed in U.S. 2014/0031242 A1, which is incorporated herein by reference. Exemplary pharmacogenomic biomarkers have been discovered to correlate with varied individual responses (e.g., efficacy, adverse effect, and other end points) to therapeutic retinoid X receptor modulator, such as bexarotene, in treating diseases such as, non-small cell lung cancer, for example, as disclosed in U.S. 2015/0368720 A1, which is incorporated herein by reference.

As used herein, the term "polymorphic locus" refers to a region in a nucleic acid at which two or more alternative nucleotide sequences are observed in a significant number of nucleic acid samples from a population of individuals. A polymorphic locus may be a nucleotide sequence of two or more nucleotides, an inserted nucleotide or nucleotide sequence, a deleted nucleotide or nucleotide sequence, or a microsatellite, for example. A polymorphic locus that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic locus is often one nucleotide in length, which is referred to herein as a "single nucleotide polymorphism" or a "SNP." In some embodiments, the high-density genotyping may be conducted by using SNPs. In some embodiments, about 1,000-5,000,000 or more SNPs, may be used. In some embodiments, the high-density genotyping may be array-based. In some embodiments, the high-density genotyping may be conducted by using sequencing, such as high-throughput sequencing.

Where there are two, three, or four alternative nucleotide sequences at a polymorphic locus, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those individuals who possess two major alleles or two minor alleles are often referred to as being "homozygous" with respect to the polymorphism, and those individuals who possess one major allele and one minor allele are normally referred to as being "heterozygous" with respect to the polymorphism. Individuals who are homozygous with respect to one allele are sometimes predisposed to a different phenotype as compared to individuals who are heterozygous or homozygous with respect to another allele.

Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense.

SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

In genetic analysis that identifies one or more pharmacogenomic biomarkers, samples from individuals having different values in a relevant phenotype often are allelotyped and/or genotyped. The term "allelotype" as used herein refers to a process for determining the allele frequency for a polymorphic variant in pooled DNA samples from cases and controls, and/or in separate DNA samples from each individual subject. By genotyping DNA from each group, an allele frequency for each locus in each group is calculated. These allele frequencies are then compared to one another. In some embodiments, DNA samples are genotyped using whole genome SNP arrays, such as those manufactured by Affymetrix (Santa Clara, Calif.) and/or Illumina (San Diego, Calif.), such as the Affymetrix 500K array. In addition to Affymetrix arrays, Illumina chips and Sequenom MassArray can also be used. Any suitable genotype calling algorithm(s) may be used. In some embodiments, the genotype calls are generated using the Robust Linear Model with the Mahalanobis Distance Classifier (RLMM) algorithm, the RLMM with a Bayesian step (BRLMM) algorithm, the Axiom™ GT1 algorithm, the BRLMM using perfect-match probes (BRLMM-P) algorithm, or the Birdseed algorithm (Rabbee et al., *Bioinformatics* (2006) 22:7-12; Korn et al., *Nat Genet* (2008) 40:1253-60).

A genotype or polymorphic variant may be expressed in terms of a "haplotype," which as used herein refers to a set of DNA variations, or polymorphisms, that tend to be inherited together. A haplotype can refer to a combination of alleles or to a set of SNPs found on the same chromosome. For example, two SNPs may exist within a gene where each SNP position includes a cytosine variation and an adenine variation. Certain individuals in a population may carry one allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

Sometimes, a polymorphic variant is reported in a database without determining whether the variant is represented in a significant fraction of a population. Because a subset of these reported polymorphic variants are not represented in a statistically significant portion of the population, some of them are sequencing errors and/or not biologically relevant. Thus, it is often not known whether a reported polymorphic variant is statistically significant or biologically relevant until the presence of the variant is detected in a population of individuals and the frequency of the variant is determined. A polymorphic variant is statistically significant (and optionally often biologically relevant) if it is represented in 1% or more of a population, sometimes 5% or more, 10% or more, 15% or more, or 20% or more of a population, and often 25% or more, 30% or more, 35% or more, 40% or more, 45% or more, or 50% or more of a population. For certain genetic diseases and/or rare diseases, however, a variant may represent a very small percentage of a population and yet is still biologically relevant.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "clinical sample" or "disease sample" and variations thereof refer to any sample obtained from a subject of interest that would be expected or is known to contain the cellular and/or molecular entity that is to be characterized.

The term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds that are not naturally intermixed with the tissue in nature such as preservatives, anticoagulants, buffers, fixatives, nutrients, antibiotics, or the like.

The biological sample herein can be a plasma, serum, whole blood, or dried blood spot sample. "Plasma," or "blood plasma," as used herein, refers to the intravascular fluid part of extracellular fluid (all body fluid outside of cells). It is mostly water and contains dissolved proteins, glucose, clotting factors, mineral ions, hormones and carbon dioxide (plasma being the main medium for excretory product transportation). Blood plasma is prepared by spinning a tube of fresh blood containing an anti-coagulant in a centrifuge until the blood cells fall to the bottom of the tube. The blood plasma is then poured or drawn off. "Blood serum" is blood plasma without fibrinogen or the other clotting factors (i.e., whole blood minus both the cells and the clotting factors).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(P)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "array" or "microarray", as used herein refers to an ordered arrangement of hybridizable array elements, such as polynucleotide probes (e.g., oligonucleotides), beads, or binding reagents (e.g., antibodies), on a substrate. The substrate can be a solid substrate, such as a glass or silica slide, a fiber optic binder, or a semi-solid substrate, such as nitrocellulose membrane. The nucleotide sequences can be DNA, RNA, or any permutations thereof.

As used herein, the term "phenotype" refers to a trait which can be compared between individuals, such as presence or absence of a condition, a visually observable difference in appearance between individuals, metabolic variations, physiological variations, variations in the function of biological molecules, and the like. A phenotype can be qualitative or quantitative. An example of a phenotype is responsiveness to a treatment, such as a drug.

"Responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) relief, to some extent, of one or more symptoms associated with the disorder; (7) increase in the length of disease-free presentation following treatment; (8) decreased mortality at a given point of time following treatment; and/or (9) lack of adverse effects following treatment. Responsiveness can also be assessed using any endpoint indicating side effect and/or toxicity to the patient.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "prediction" or "prognosis" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example an antibody raised against an immune complex of a second antibody and its corresponding antigen may be considered to be an SBP member for the immune complex.

As used herein, the term "homologue" is used to refer to a nucleic acid which differs from a naturally occurring nucleic acid (i.e., the "prototype" or "wild-type" nucleic acid) by minor modifications to the naturally occurring nucleic acid, but which maintains the basic nucleotide structure of the naturally occurring form. Such changes include, but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "complementary" or "matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5× Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5× Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5× Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, the term "output" refers to a value or score generated from a computer algorithm. The output may be generated based on assay results using the biomarkers disclosed herein as inputs to the computer algorithm. An "output" can be either quantitative or qualitative, and can be used for determining the likely responsiveness of a subject to a treatment in a companion diagnostic test.

A companion diagnostic test or method generally provides information that is essential for the safe and effective use of a corresponding drug or biological product. The test helps a health care professional determine whether a particular therapeutic product's benefits to patients will outweigh any potential serious side effects or risks. In certain aspects, a companion diagnostic test disclosed herein can identify patients who are most likely to benefit from a particular therapeutic agent, such as an acyclic bisindolylmaleimide (e.g., enzastaurin (LY317615)); identify patients likely to be at increased risk for serious side effects as a result of treatment with a particular therapeutic agent; and/or monitor response to treatment with a particular therapeutic agent for the purpose of adjusting treatment to achieve improved safety or effectiveness. Companion diagnostics may be co-developed with one or more drugs (or a combination therapy such as a cocktail) to aid in selecting or excluding patient groups for treatment with that particular drug on the basis of their biological characteristics that determine responders and non-responders to the therapy. In some aspects, companion diagnostics are developed based on companion biomarkers, biomarkers that prospectively help predict likely response or severe toxicity. In some embodiments, the present disclosure provides a companion biomarker comprising one or more, for example, 1, 2, 3, 4, 5, 6, 7, 8, 9, 10, or more of the SNPs disclosed herein.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

C. Biomarkers for Predicting Enzastaurin Responsiveness

Enzastaurin (LY317615), an acyclic bisindolylmaleimide, is a potent and selective inhibitor of protein kinase C beta (PKCβ; half maximal inhibitory concentration [IC50] approximately 6 nM), as well as other PKC isoforms (e.g., α, γ, ε, $IC_{50}$s 40-100 nM) (Graff et al. 2005) and other AGC-family kinases including p90RSK and MSK (Parsons et al. 2008). In cultured cancer cells (e.g., colon, non-small cell lung cancer [NSCLC], glioblastoma, diffuse large B-cell and cutaneous T-cell lymphoma, multiple myeloma, and Waldenstrom's macroglobulinemia), enzastaurin treatment at clinically relevant concentrations blocks intracellular signaling through the PKC and PI3K/AKT pathways, specifically suppressing phosphorylation of AKT, mammalian target of rapamycin, p70S6K, ribosomal protein S6, 4EBP1, cAMP response element-binding protein, and GSK3β. Accordingly, enzastaurin inhibits tumor cell proliferation, induces tumor cell apoptosis (i.e., programmed cell death), and suppresses tumor-induced angiogenesis (Graff et al. 2005; Querfeld et al. 2006; Rizvi et al. 2006; Neri et al. 2008; Parsons et al. 2008). By blocking these signaling pathways, enzastaurin also blunts the response of endothelial cells to angiogenic stimuli (e.g., VEGF) (McNulty et al. 2008).

Oral dosing with enzastaurin (to achieve plasma exposure levels similar to those in human clinical trials) suppresses VEGF induced angiogenesis in the rat corneal micropocket model. Single-agent enzastaurin treatment also suppresses growth of multiple human cancer xenografts, including colorectal carcinomas, glioblastomas (Graff et al. 2005), diffuse large B-Cell lymphomas (Rossi et al. 2005), Waldenstrom's macroglobulinemia, and multiple myeloma (Moreau et al. 2007; Podar et al. 2007). Enzastaurin treatment enhances the activity of radiation in pancreatic cancer (Spalding et al. 2007), metastatic breast cancer (Dudek et al. 2008), and intracranially implanted glioblastomas (Tabatabai et al. 2007). Similarly, enzastaurin enhances the efficacy of numerous targeted agents, including sunitinib in renal cell carcinoma (McNulty et al. 2008) and bortezomib in multiple myeloma (Podar et al. 2007). By suppressing signaling through the AKT pathway, which is frequently involved in chemoresistance (West et al. 2002), enzastaurin also potentiates the activity of oncolytics, such as temozolomide in glioblastoma (Parsons et al. 2008). The antitumor activity of enzastaurin reflects multiple mechanisms of action: a direct effect on tumor cells (suppression of tumor cell proliferation, and the induction of tumor cell death), and an indirect effect on tumor-associated endothelial cells (suppression of tumor-induced angiogenesis).

Enzastaurin has been tested in more than 60 clinical studies including many different types of tumors such as lymphoma, leukemia, brain cancer, lung cancer, breast cancer, prostate cancer, colon cancer etc. As of 13 Sep. 2013, a total of 4387 cancer patients and healthy subjects have been enrolled in Eli Lilly and Company-sponsored clinical trials, of whom approximately 3337 individuals received enzastaurin. Of the approximately 3337 individuals who received enzastaurin, 3149 were cancer patients and 188 were healthy subjects in 9 completed clinical pharmacology studies. In 2014, Denovo Biopharma LLC (Denovo) completed the transfer of ownership of Enzastaurin to enable its further clinical development. Denovo is identifying unique subsets of patients who have responded favorably to enzastaurin, and will continue the clinical development of enzastaurin for the treatment of cancers such as DLBCL and glioma/glioblastoma, in selected sub-populations of patients more likely to respond to enzastaurin.

In one aspect, the present disclosure provides a method of predicting responders to a therapeutic regime which includes enzastaurin and/or other PKCβ and other AGC kinases (such as GSKs, p90RSKs, MSKs, GSK3β) inhibitors, by using results generated by genotyping the genetic biomarkers.

Enzastaurin (LY317615) is an oral serine/threonine kinase inhibitor that selectively targets PKCβ suppressing signaling through the phosphotidyl-inositol 3 kinase/protein kinase B (PI3K/AKT) pathway, decreasing tumor proliferation, and inducing apoptosis in cancer cells. Based on early phase clinical data, enzastaurin was shown to be well tolerated using daily oral dosing. Enzastaurin's anti-tumor activity has been tested in a large number of clinical studies, particularly in DLBCL and glioma/glioblastoma/central nervous system (CNS) tumors.

Enzastaurin is a PKC Beta selective inhibitor. Enzastaurin has the chemical name 3-(1-methyl-1H-indol-3-yl)-4-[1-[1-(pyridin-2-ylmethyl)piperidin-4-yl]-1H-indol-3-yl]-1H-pyrrole-2,5-dione and is disclosed in U.S. Pat. No. 5,668,152. Any pharmaceutically acceptable salt of enzastaurin is also within the present disclosure and can be used in the composition and/or method disclosed herein. For example, U.S. Pat. No. 8,114,901 discloses a crystalline 2,5-dione-3-(1-methyl-1H-indol-3-yl)-4-[1-[1-(pyridin-2-ylmethyl)piperidin-4-yl]-1H-indol-3-yl]-1H-pyrrole mono-hydrochloride or a hydrate thereof. A pharmaceutical composition comprising enzastaurin or a salt thereof and a pharmaceutical carrier is also within the present disclosure.

Figure 1A:
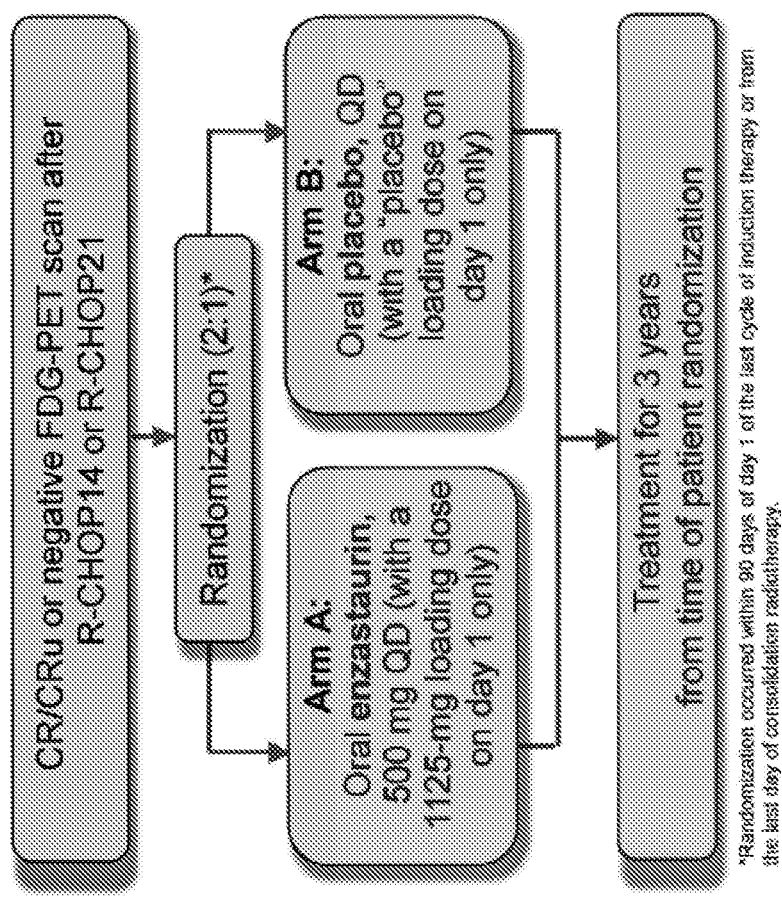

Prelude trial is a multicenter, phase 3, randomized, double-blind, placebo-controlled trial enrolled patients at high risk of recurrence following rituximab-cyclophosphamide, doxorubicin, vincristine, and prednisone (R-CHOP). Seven hundred fifty-eight patients with stage 2 bulky or stage 3-4 DLBCL, 3 or more International Prognostic Index (IPI) risk factors at diagnosis, and a confirmed response (CR)/unconfirmed complete response (CRu) following R-CHOP were assigned 2:1 to receive oral enzastaurin 500 mg daily or placebo for 3 years or until disease progression or unacceptable toxicity. Primary endpoint was DFS 3 years after the last patient entered treatment (FIG. 1A). Although enzastaurin failed to demonstrate statistically significant efficacy overall patient population (FIG. 1B), it is disclosed herein that a subset of patients who experienced chromaturia with exhibited significant anti-tumor activity in DLBCL in PRELUDE trial (FIG. 1C). By this analysis, the patients experiencing chromaturia after enzastaurin treatment exhibiting significantly longer overall survival than that of the control group (Hazard Ratio=0.46 and p-value=0.025). Thus, chromaturia itself could be a biomarker predicting enzastaurin efficacy, however, chromaturia only can be observed after patients taking enzastaurin. The pharmacogenomic biomarker which can predict enzastaurin efficacy would be more desirable as these biomarkers can be used to identify potential enzastaurin responders before taking the drugs.

Unlike most oncology biomarker studies focusing on mutations or target protein overexpression in tumor cells, germline genetic polymorphisms also contribute to the various responses to the same drug in different patients. Thus, germline DNA samples extracted from blood of patients enrolled in Prelude trial were used to identify pharmacogenetic biomarker for enzastaurin. In discovery phase, 282 samples from enzastaurin treatment group (95 were from patients with chromaturia and 187 were from patients without chromaturia) were genotyped using the whole genome single nucleotide polymorphism (SNP) arrays from Illumina, which contain about 5 million SNPs.

It was found that a specific configuration for two SNPs located on chromosome 8, Reference SNP ID 309605 (rs309605) and Reference SNP ID 309604 (rs309604), was strongly associated with survival in the enzastaurin arm. Patients with heterozygous or homozygous for the presence of a thymidine at both rs309605 and rs309604 had significantly improved survival in enzastaurin treated arm (FIG. 2A). In one embodiment, the presence of a thymidine at rs309605 (homozygous or heterozygous) and a thymidine at rs309604 (homozygous or heterozygous) in the same subject will cause the subject to be classified as "biomarker positive" and the presence of cytidine (homozygous) at either SNP will cause the subject to be classified as "biomarker negative."

It was identified that rs309605 and rs309604 were strongly associated with enzastaurin anti-tumor activity as patients carrying A allele of rs309605 and rs309604 (AA+AB genotype) exhibited significant longer overall survival comparing to patient carrying BB genotype. For both rs309605 and rs309604, allele A represents T and allele B represents C. Among patients who had events, there are 22 carrying BB genotypes vs 31 carrying AA+AB. Among patients who survived, there are 22 BB carrying genotype patients vs 209 patients carrying AA+AB genotypes, which gives a p-value $5.75 \times 10^{-9}$. A p-value smaller than $5 \times 10^{-8}$ is usually considered the threshold for genome-wide significance. Since rs309605 and rs309604 are in linkage disequilibrium, the results from rs309605 is used here as an example. The prediction of enzastaurin using rs309605 on overall survival in these DLBCL patients is shown in FIG. 2A.

To examine whether rs309605 is merely a prognostic biomarker, DNA samples from 238 patients from placebo control group were genotyped at rs309605 using the Taqman SNP assays. FIG. 2B shows that there is no significant difference in overall survival between patients carrying AA+AB genotype vs patients carrying BB genotype. Therefore, rs309605 associated improvement in survival is related to enzastaurin treatment, and rs309605 appears to be a pharmacogenomics biomarker for predicting enzastaurin anti-tumor activity.

As both rs309605 and chromaturia are associated with enzastaurin's anti-tumor activity, the interaction between these two biomarkers was next examined FIG. 2C shows that patients carrying AA+AB genotype at rs309605 with chromaturia exhibit the best overall survival and the interaction is between the two biomarkers are statistically significant (p value=0.017, Table 3). In some aspects of the present disclosure, like what is observed in DLBCL prelude trial, the predicative power for enzastaurin responsiveness is even better when rs309605 is combined with chromaturia (Table 3). In addition, DNA from 177 patients from enzastaurin treated patients without chromaturia was genotyped, and there was no significant difference in overall survival between patients carrying AA+AB genotypes vs. patients carry BB genotypes, this result may partially explained by the lack of chromaturia in this subset of patients.

Next it was examined whether the association between rs309605 and enzastaurin activity is unique to DLBCL patients under the maintenance mode (Prelude trial), DNA samples from patient enrolled in S028 trials, where enzastaurin was tested in $1^{st}$ line setting in combination with R-CHOP (FIG. 3A), was genotyped at rs309605 using Taqman assay. Although there is no significant difference between the enzastaurin arm and the control arm in general patient population (FIG. 3B), FIG. 3C shows that patients carrying AA or AB at rs309605 (AA+AB) also exhibited significant better survival than patient carrying BB genotype in enzastaurin treatment arm, and rs309605 genotype has little impact on overall survival of patients in control arm when R-CHOP along was administrated (FIG. 3D). This result confirms that rs309605 as pharmacogeonomic biomarker for enzastaurin activity in DLBCL under two very different trial design. In one aspect, since there are only five patients were reported having experienced chromaturia, it may not provide meaningful result to examine the interaction between chromaturia and rs309605 in this phase 2 DLBCL trial. In one aspect, the low incidence of chromaturia in this trial may be due to the under-reporting as chromaturia was not key clinical outcome required to record under original protocol. In one aspect, patients having IPI>2 experienced better survival from enzastaurin treatment. Thus, subgroup analysis was conducted using both IPI and rs309605 and rs309604. FIGS. 3E-3F show that patient carrying AA+AB at rs309605 and rs309604 and having IPI>2 exhibited superior efficacy in both overall survival (FIG. 3E) and Progression Free (PFS) survival (FIG. 3F), particularly the hazard ratio of overall survival reached to 0.28 in favor of the enzastaurin treatment arm.

To verify the genotype results from these archived clinical samples, some of the samples were genotyped by more than one technology, such as Illumina SNP arrays, Taqman Assay, and Sequencing, and they mostly generated identical results. In addition, these DNA samples were also genotyped at rs309604, and similar results to those at rs309605 were observed.

Because the biomarker identified herein for enzastaurin is germline genetic polymorphisms instead of mutations or target overexpression in tumor cells, which may associated with specific tumor type, this same genetic polymorphism, rs309605, might be a potential pharmacogenetics biomarkers for enzastaurin efficacy in other tumor types too. The DNA samples from blood of GBM patients in S008 trials were used to genotype rs309605 by Taqman assay. FIG. 4A shows that patients carrying AA or AB genotype at rs309605 demonstrate better overall survival comparing to patients carrying BB genotypes. The correlation between chromaturia and enzastaurin's efficacy was also examined FIG. 4B shows that GBM patients experiencing chromaturia has significant improved survival vs. those without chromaturia.

Biological plausibility of the genomic biomarker and its potential mechanism provide further consideration of these effects. The gene closest to rs309605 and rs309604 is TRPS1, which encodes Transcriptional repressor GATA binding 1 or Tricho-Rhino-Phalangeal Syndrome Type I Protein (FIG. 5B). TRPS1 represses GATA-regulated genes and plays a central role in cell cycle control and tumor development. Enzastaurin is a potent inhibitor for PKC-β, PI3K, and AKT, which are also known to be involved in cell cycle regulation as well as interact with GATA factors directly and indirectly. However, the precise mechanism by which these SNPs affect enzastaurin and its effect on survival remains to be elucidated.

Thus, in one aspect, described herein is one or more novel genomic biomarkers that correlate with the activity of a kinase inhibitor, such as enzastaurin. These biomarkers can be used to identify the patients who are most likely to benefit or experience adverse effect from the kinase inhibitor (such as enzastaurin) treatment.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon).

In one aspect, the biomarkers of the invention are rs309605 and those provided in Tables 1A to 1H and Table 2, and others in linkage disequilibrium with them, and complementary sequences thereof. For example, in CEU and CHB populations, the minor allele of the following SNPs is designated allele B, and the major allele is designated allele A.

Marker rs309605 (e.g., as shown in SEQ ID NO: 1 or a complementary sequence thereof): TGGGGAATGTCAT-TCCATGTTAGGC[A/G]TCATGTTGAAACATATTATTT-CAT A. The SNP can be retrieved from NCBI, available at ncbi.nlm.nih.gov/projects/SNP/snp_ref.cgi?rs=309605. The above sequence is in reverse orientation and the forward orientation is TATGAAATAATATGTTTCAACATGA[C/T] GCCTAACATGGAATGACATTCCCCA. The allele frequency table uses the forward orientation in which the variation site is [C/T].

|  | Allele | HGVS Names |
|---|---|---|
| Variation Class: | SNV: single nucleotide variation | NC_000008.10:g.116129344C > T<br>NC_000008.11:g.115117115C > T |
| RefSNP Alleles: | A/G (REV) | |
| Ancestral Allele: | G | |
| MAF/MinorAlleleCount: | C = 0.4285/2146 (1000 Genomes)<br>C = 0.4426/12889 (TOPMED) | |

Marker rs309604 (e.g., as shown in SEQ ID NO: 2 or a complementary sequence thereof): GAAGGAACACTTTCCCTAATGCCA[C/T] GAAGGAACAAGGATTCTGATAGC TT. The SNP can be retrieved from NCBI, available at ncbi.nlm.nih.gov/projects/SNP/snp_ref.cgi?rs=309604.

|  | Allele | HGVS Names |
|---|---|---|
| Variation Class: | SNV: single nucleotide variation | NC_000008.10:g.116130309C > T<br>NC_000008.11:g.115118080C > T |
| RefSNP Alleles: | C/T (FWD) | |
| Ancestral Allele: | C | |
| MAF/MinorAlleleCount: | C = 0.4287/2147 (1000 Genomes)<br>C = 0.4428/12893 (TOPMED) | |

For both rs309605 and rs309604, allele A represents T and allele B represents C at the SNP site.

Marker rs5894240 (e.g., as shown in SEQ ID NO: 3 or a complementary sequence thereof): AAAAGCAAAAAAAAAATAAAAAAAT[-/A] AAAAAAAAAAGGCAAAGAGACAGAA. The SNP can be retrieved from NCBI, available at ncbi.nlm.nih.gov/projects/SNP/snp_ref.cgi?rs=5894240.

|  | Allele | HGVS Names |
|---|---|---|
| Variation Class: | DIV: deletion/insertion variation | NC_000008.10:g.116130397delA<br>NC_000008.11:g.115118168delA |
| RefSNP Alleles: | —/A (FWD) | |
| Ancestral Allele: | A | |
| MAF/MinorAlleleCount: | A = 0.3644/1825 (1000 Genomes) | |

Marker rs1494748 (e.g., as shown in SEQ ID NO: 4 or a complementary sequence thereof): CACCCCGT-TAAAAAAAAAAAAAAATC[G/T]GTCACTAAT-TGTTCCGGTTACTA TT. The SNP ran be retrieved from NCBI, available at ncbi.nlm.nih.gov/projects/SNP/snp_ref.cgi?rs=1494748.

|                      | Allele                              | HGVS Names                                                       |
|----------------------|-------------------------------------|------------------------------------------------------------------|
| Variation Class:     | SNV: single nucleotide variation    | NC_000008.10:g.116132779G > T<br>NC_000008.11:g.115120550G > T   |
| RefSNP Alleles:      | G/T (FWD)                           |                                                                  |
| Ancestral Allele:    | G                                   |                                                                  |
| MAF/MinorAlleleCount:| G = 0.4295/2151 (1000 Genomes)<br>G = 0.4433/12909 (TOPMED) |                                          |

Marker rs7836309, (e.g., as shown in SEQ ID NO: 5 or a complementary sequence thereof): atagcaataggcaacaaacaaacta[G/T]caaatatagtgtcaagtaccaaaag. The SNP can be retrieved from NCBI, available at ncbi.nlm.nih.gov/projects/SNP/snp_ref.cgi?rs=7836309.

|                      | Allele                              | HGVS Names                                                       |
|----------------------|-------------------------------------|------------------------------------------------------------------|
| Variation Class:     | SNV: single nucleotide variation    | NC_000008.10:g.116154006T > G<br>NC_000008.11:g.115141777T > G   |
| RefSNP Alleles:      | G/T (FWD)                           |                                                                  |
| MAF/MinorAlleleCount:| G = 0.4575/2291 (1000 Genomes)<br>G = 0.4818/14029 (TOPMED) |                                          |

Marker rs309607 (e.g., as shown in SEQ ID NO: 6 or a complementary sequence thereof): CATTCTCATCAT-AGTCTGCTTCTCA[C/T]TTGATTCAGTATTGGAT-GAAGATC A. The SNP can be retrieved from NCBI, available at ncbi.nlm.nih.gov/projects/SNP/snp_ref.cgi?rs=309607.

|                      | Allele                              | HGVS Names                                                       |
|----------------------|-------------------------------------|------------------------------------------------------------------|
| Variation Class:     | SNV: single nucleotide variation    | NC_000008.10:g.116118689G > A<br>NC_000008.11:g.115106460G > A   |
| RefSNP Alleles:      | C/T (REV)                           |                                                                  |
| Ancestral Allele:    | C                                   |                                                                  |
| MAF/MinorAlleleCount:| G = 0.4393/2200 (1000 Genomes)<br>G = 0.4559/13274 (TOPMED) |                                          |

Marker rs2132025 (e.g., as shown in SEQ ID NO: 7 or a complementary sequence thereof): GCTCTATTT-TATAAAAGTCTATTAA[C/T]TTTAACTGAAAT-CAAAATAACTAC A. The SNP can be retrieved from NCBI, available at ncbi.nlm.nih.gov/projects/SNP/snp_ref.cgi?rs=2132025.

|                      | Allele                              | HGVS Names                                                       |
|----------------------|-------------------------------------|------------------------------------------------------------------|
| Variation Class:     | SNV: single nucleotide variation    | NC_000008.10:g.116146327C > T<br>NC_000008.11:g.115134098C > T   |
| RefSNP Alleles:      | C/T (FWD)                           |                                                                  |
| Ancestral Allele:    | T                                   |                                                                  |

|  | Allele | HGVS Names |
| --- | --- | --- |
| MAF/MinorAlleleCount: | T = 0.4511/2259 (1000 Genomes) G = 0.4725/13757 (TOPMED) | |

Marker rs11990158 (e.g., as shown in SEQ ID NO: 8 or a complementary sequence thereof): tgaatttcatc-caaagcctttctg[G/T]atctatttagataataatgtggttt. The SNP can be retrieved from NCBI, available at ncbi.nlm.nih.gov/projects/SNP/snp_ref.cgi?rs=11990158.

|  | Allele | HGVS Names |
| --- | --- | --- |
| Variation Class: | SNV: single nucleotide variation | NC_000008.10:g.116150758G > T NC_000008.11:g.115138529G > T |
| RefSNP Alleles: | G/T (FWD) | |
| Ancestral Allele: | T | |
| MAF/MinorAlleleCount: | T = 0.3690/1848 (1000 Genomes) G = 0.3512/10225 (TOPMED) | |

Marker rs6469570 (e.g., as shown in SEQ ID NO:9 or a complementary sequence thereof): atccaaagcctttctggatctatt[G/T]agataataatgtggttttgtctt. The SNP can be retrieved from NCBI, available at ncbi.nlm.nih.gov/projects/SNP/snp_ref.cgi?rs=6469570.

|  | Allele | HGVS Names |
| --- | --- | --- |
| Variation Class: | SNV: single nucleotide variation | NC_000008.10:g.116150766T > G NC_000008.11:g.115138537T > G |
| RefSNP Alleles: | G/T (FWD) | |
| Ancestral Allele: | G | |
| MAF/MinorAlleleCount: | G = 0.4551/2279 (1000 Genomes) G = 0.4752/13836 (TOPMED) | |

Marker rs309603 (e.g., as shown in SEQ ID NO: 10 or a complementary sequence thereof): CTACAGACCAAGT-GAACAACAGAGG[A/C]CTGCTGAATTCATTCATTG-CATT TT. The SNP can be retrieval from NCBI, available at ncbi.nlm.nih.gov/projects/SNP/snp_ref.cgi?rs=309603.

|  | Allele | HGVS Names |
| --- | --- | --- |
| Variation Class: | SNV: single nucleotide variation | NC_000008.10:g.116122316T > G NC_000008.11:g.115110087T > G |
| RefSNP Alleles: | A/C (REV) | |
| Ancestral Allele: | C | |
| MAF/MinorAlleleCount: | T = 0.3349/1677 (1000 Genomes) G = 0.3430/9988 (TOPMED) | |

Marker rs923967 (e.g., as shown in SEQ ID NO: 11 or a complementary sequence thereof): AACTTGGGGCACTCTGCACTACTGC[A/T]TGCCAG-CATTTTAAAAAGTCATC AG. The SNP can be retrieved from NCBI, available at ncbi.nlm.nih.gov/projects/SNP/snp_ref.cgi?rs=923967.

|  | Allele | HGVS Names |
| --- | --- | --- |
| Variation Class: | SNV: single nucleotide variation | NC_000008.10:g.116153312T > A<br>NC_000008.11:g.115141083T > A |
| RefSNP Alleles: | A/T (FWD) |  |
| Ancestral Allele: | T |  |
| MAF/MinorAlleleCount: | A = 0.2730/1367 (1000 Genomes)<br>G = 0.3146/9160 (TOPMED) |  |

Marker rs1494751 (e.g., as shown in SEQ ID NO: 12 or a complementary sequence thereof): CATACAC-CAAGAGTTTTATAAATAA[A/G]TTTATTTCAATAT-GAAGGTTAAA TT. The SNP can be retrieved from NCBI, available at ncbi.nlm.nih.gov/projects/SNP/snp_ref.cgi?rs=149475.

|  | Allele | HGVS Names |
| --- | --- | --- |
| Variation Class: | SNV: single nucleotide variation | NC_000008.10:g.116114984A > G<br>NC_000008.11:g.115102755A > G |
| RefSNP Alleles: | A/G (FWD) |  |
| Ancestral Allele: | A |  |
| MAF/MinorAlleleCount: | A = 0.4387/2197 (1000 Genomes)<br>G = 0.4584/13349 (TOPMED) |  |

Marker rs2575943 (e.g., as shown in SEQ ID NO: 13 or a complementary sequence thereof): TTAATCG-GAATGCTCCCTGCTCCTC[A/T]CTTTATTCCCTAGA-TAAACGTACA C. The SNP can be retrieved from NCBI, available at ncbi.nlm.nih.gov/projects/SNP/snp_ref.cgi?rs=2575943.

|  | Allele | HGVS Names |
| --- | --- | --- |
| Variation Class: | SNV: single nucleotide variation | NC_000008.10:g.116114084A > T<br>NC_000008.11:g.115101855A > T |
| RefSNP Alleles: | A/T (REV) |  |
| Ancestral Allele: | T |  |
| MAF/MinorAlleleCount: | A = 0.4411/2209 (1000 Genomes)<br>G = 0.4598/13389 (TOPMED) |  |

Marker rs167446 (e.g., as shown in SEQ ID NO: 14 or a complementary sequence thereof): atatcatttacattagcaacctcta[A/G]aataaaatatttaggtattagccta. The SNP can be retrieved from NCBI, available at ncbi.nlm.nih.gov/projects/SNP/snp_ref.cgi?rs=167446.

| | Allele | HGVS Names |
|---|---|---|
| Variation Class: | SNV: single nucleotide variation | NC_000008.10:g.116101925T > C<br>NC_000008.11:g.115089696T > C |
| RefSNP Alleles: | A/G (REV) | |
| Ancestral Allele: | A | |
| MAF/MinorAlleleCount: | T = 0.4217/2112 (1000 Genomes)<br>T = 0.4350/12665 (TOPMED) | |

Marker rs309606 (e.g., as shown in SEQ ID NO: 15 or a complementary sequence thereof): CTATTATTTTCAGAA-CATTGCTTAA[C/T]ATGTTGGTTGAGTCCGGCA-GACAAA. The SNP can be retrieved from NCBI, available at ncbi.nlm.nih.gov/projects/SNP/snp_ref.cgi?rs=309606.

| | Allele | HGVS Names |
|---|---|---|
| Variation Class: | SNV: single nucleotide variation | NC_000008.10:g.116126138G > A<br>NC_000008.11:g.115113909G > A |
| RefSNP Alleles: | C/T (REV) | |
| Ancestral Allele: | T | |
| MAF/MinorAlleleCount: | G = 0.1623/813 (1000 Genomes)<br>G = 0.2037/5930 (TOPMED) | |

Marker rs72675965 (e.g., as shown in SEQ ID NO: 16 or a complementary sequence thereof): TTTATTGAAATACT-TAAATTTACTA[C/T]TGTAAATACTTTTATACTTT-TATAT. The SNP can be retrieved from NCBI, available at ncbi.nlm.nih.gov/projects/SNP/snp_ref.cgi?rs=72675965.

| | Allele | HGVS Names |
|---|---|---|
| Variation Class: | SNV: single nucleotide variation | NC_000008.10:g.116147352C > T<br>NC_000008.11:g.115135123C > T |
| RefSNP Alleles: | C/T (FWD) | |
| Ancestral Allele: | C | |
| MAF/MinorAlleleCount: | T = 0.1563/783 (1000 Genomes)<br>T = 0.1909/5558 (TOPMED) | |

Marker rs309602 (e.g., as shown in SEQ ID NO. 17 or a complementary sequence thereof): gacctaggagctccc-caagccaggg[C/T]tgtgacaccgtctttggggatctct. The SNP can be retrieved from NCBI, available at ncbi.nlm.nih.gov/projects/SNP/snp_ref.cgi?rs=309602.

| | Allele | HGVS Names |
|---|---|---|
| Variation Class: | SNV: single nucleotide variation | NC_000008.10:g.116123220A > G<br>NC_000008.11:g.115110991A > G |
| RefSNP Alleles: | C/T (REV) | |
| Ancestral Allele: | C | |

-continued

| | Allele | HGVS Names |
|---|---|---|
| MAF/MinorAlleleCount: | T = 0.1577/790 (1000 Genomes) A = 0.1995/5808 (TOPMED) | |

Marker rs309608 (e.g., as shown in SEQ ID NO: 18 or a complementary sequence thereof): TCCATTTAAAATTAT-CACGCTTCTT[C/T]TTCTCTACTCGTCAACATC-CAACA C. The SNP can be retrieved from NCBI, available at ncbi.nlm.nih.gov/projects/SNP/snp_ref.cgi?rs=309608.

| | Allele | HGVS Names |
|---|---|---|
| Variation Class: | SNV: single nucleotide variation | NC_000008.10:g.116117012G > A NC_000008.11:g.115104783G > A |
| RefSNP Alleles: | C/T (REV) | |
| Ancestral Allele: | T | |
| MAF/MinorAlleleCount: | G = 0.1591/797 (1000 Genomes) G = 0.2003/5833 (TOPMED) | |

Marker rs309610 (e.g., as shown in SEQ ID NO: 19 or a complementary sequence thereof): CAGAAC-CAAGAACTTTTCTGACCTC[C/T]TCCTGTTTCTTCCCCTAAGTGCCA G. The SNP can be retrieved from NCBI, available at ncbi.nlm.nih.gov/projects/SNP/snp_ref.cgi?rs=309610.

| | Allele | HGVS Names |
|---|---|---|
| Variation Class: | SNV: single nucleotide variation | NC_000008.10:g.116116608A > G NC_000008.11:g.115104379A > G |
| RefSNP Alleles: | C/T (REV) | |
| Ancestral Allele: | C | |
| MAF/MinorAlleleCount: | A = 0.1587/795 (1000 Genomes) A = 0.1995/5809 (TOPMED) | |

Marker rs2575911 (e.g., as shown in SEQ ID NO: 20 or a complementary sequence thereof): TCGTTCACAATTC-TACCTTATGACA[A/G]GGTCAGAAACAGAACAT-AGTAGA TG. The SNP can be retrieved from NCBI, available at ncbi.nlm.nih.gov/projects/SNP/snp_ref.cgi?rs=2575911.

| | Allele | HGVS Names |
|---|---|---|
| Variation Class: | SNV: single nucleotide variation | NC_000008.10:g.116121434T > C NC_000008.11:g.115109205T > C |
| RefSNP Alleles: | A/G (REV) | |
| Ancestral Allele: | G | |
| MAF/MinorAlleleCount: | T = 0.1573/788 (1000 Genomes) T = 0.1994/5805 (TOPMED) | |

Marker rs309609 (e.g., as shown in SEQ ID NO: 21 or a complementary sequence thereof): ATTATTATCTTCCAT-ATTAAATACA[A/G]GTTTCCTTTGTTGGGGCTCAGAAA A. The SNP can be retrieved from NCBI, available at ncbi.nlm.nih.gov/projects/SNP/snp_ref.cgi?rs=309609.

|  | Allele | HGVS Names |
| --- | --- | --- |
| Variation Class: | SNV: single nucleotide variation | NC_000008.10:g.116116736T > C<br>NC_000008.11:g.115104507T > C |
| RefSNP Alleles: | A/G (REV) |  |
| Ancestral Allele: | G |  |
| MAF/MinorAlleleCount: | T = 0.1575/789 (1000 Genomes)<br>T = 0.1991/5798 (TOPMED) |  |

Marker rs170132 (e.g., as shown in SEQ ID NO: 22 or a complementary sequence thereof): gaaaaatccatcactttcctatata[C/T]tagcaataaacatgtggaatttgaa. The SNP can be retrieved from NCBI, available at ncbi.nlm.nih.gov/projects/SNP/snp_ref.cgi?rs=170132.

|  | Allele | HGVS Names |
| --- | --- | --- |
| Variation Class: | SNV: single nucleotide variation | NC_000008.10:g.116101988A > G<br>NC_000008.11:g.115089759A > G |
| RefSNP Alleles: | C/T (REV) |  |
| Ancestral Allele: | T |  |
| MAF/MinorAlleleCount: | A = 0.4265/2136 (1000 Genomes)<br>A = 0.4410/12842 (TOPMED) |  |

Marker rs386413735 (e.g., as shown in SEQ ID NO: 23 or a complementary sequence thereof): GGCAACAAGAGTGAAACTTCATCTC[-/AA]AAAAAAAAAAAAAAAAAAAGCTGAA. The marker can be retrieved from NCBI, available at ncbi.nlm.nih.gov/projects/SNP/snp_ref.cgi?rs=386413735.

|  | Allele | HGVS Names |
| --- | --- | --- |
| Variation Class: | DIV: deletion/insertion variation | NC_000008.10:g.116120509_116120510delAA<br>NC_000008.11:g.115108280_115108281delAA |
| RefSNP Alleles: | —/AA (FWD) |  |
| MAF/MinorAlleleCount: | A = 0.2360/1182 (1000 Genomes) |  |

Marker rs2642789 (e.g., as shown in SEQ ID NO: 24 or a complementary sequence thereof): CACAGGTTGTGGT-GAGCCGAGATCC[C/T]TCCATTGTACTCATTGCAT-TCCAG C. The SNP can be retrieved from NCBI available at ncbi.nlm.nih.gov/projects/SNP/snp_ref.cgi?rs=2642789.

|  | Allele | HGVS Names |
| --- | --- | --- |
| Variation Class: | SNV: single nucleotide variation | NC_000008.10:g.116111293T > C<br>NC_000008.11:g.115089696T > C |

| Allele | | HGVS Names |
|---|---|---|
| RefSNP Alleles: | C/T (FWD) | |
| Ancestral Allele: | C | |
| MAF/MinorAlleleCount: | T = 0.1625/814 (1000 Genomes) T = 0.2043/5948 (TOPMED) | |

Marker rs2642788 (e.g., as shown in SEQ ID NO: 25 or a complementary sequence thereof): GCACAGGTTGTGGTGAGCCGAGATC[A/C]TTCCAT-TGTACTCATTGCATTCC AG. The SNP can be retrieved from NCBI available at ncbi.nlm.nih.gov/projects/SNP/snp_ref.cgi?rs=2642788.

| | Allele | HGVS Names |
|---|---|---|
| Variation Class: | SNV: single nucleotide variation | NC_000008.10:g.116111292C > A NC_000008.11:g.115099063C > A |
| RefSNP Alleles: | A/C (FWD) | |
| Ancestral Allele: | G | |
| MAF/MinorAlleleCount: | C = 0.1625/814 (1000 Genomes) C = 0.2044/5952 (TOPMED) | |

Marker rs2575944 (e.g., as shown in SEQ ID NO: 26 or a complementary sequence thereof): AAAACCAAAC-CAAAGACTGAGAAAT[G/T]ATTAGAAGCCACTG-GAAGTTTT TTA. The SNP can be retrieved from NCBI, available at ncbi.nlm.nih.gov/projects/SNP/snp_ref.cgi?rs=2575944.

| | Allele | HGVS Names |
|---|---|---|
| Variation Class: | SNV: single nucleotide variation | NC_000008.10:g.116101925A > C NC_000008.11:g.115089696A > C |
| RefSNP Alleles: | G/T (REV) | |
| Ancestral Allele: | G | |
| MAF/MinorAlleleCount: | A = 0.1567/785 (1000 Genomes) A = 0.2000/5823 (TOPMED) | |

Marker rs309614 (e.g., as shown in SEQ ID NO: 27 or a complementary sequence thereof): ATTTATC-CAAATGCCTTTCCATGGC[A/G]TTCACTGAGCAAAT-TCTGGATTTT T. The SNP can be retrieved from NCBI, available at ncbi.nlm.nih.gov/projects/SNP/snp_ref.cgi?rs=309614.

| | Allele | HGVS Names |
|---|---|---|
| Variation Class: | SNV: single nucleotide variation | NC_000008.10:g.116106473C > T NC_000008.11:g.115094244C > T |
| RefSNP Alleles: | A/G (REV) | |
| Ancestral Allele: | A | |
| MAF/MinorAlleleCount: | C = 0.1565/784 (1000 Genomes) C = 0.2000/5825 (TOPMED) | |

Marker rs309601 (e.g., as shown in SEQ ID NO: 28 or a complementary sequence thereof): TTTCCATGTA-GACAGAAGAATGAGG[A/T]GC-TACCCTAGTGTGTCCCTTAAT GA. The SNP can be retrieved from available at ncbi.nlm.nih.gov/projects/SNP/snp_ref.cgi?rs=309601.

|  | Allele | HGVS Names |
|---|---|---|
| Variation Class: | SNV: single nucleotide variation | NC_000008.10:g.116124691T > A<br>NC_000008.11:g.115112462T > A |
| RefSNP Alleles: | A/T (REV) |  |
| Ancestral Allele: | A |  |
| MAF/MinorAlleleCount: | T = 0.4657/2332 (1000 Genomes)<br>A = 0.4752/13836 (TOPMED) |  |

The invention includes individual biomarker and biomarker sets. The invention also includes other biomarkers, e.g., SNPs, which have high correlation with the biomarkers, and they could also be used to predict enzastaurin responses by patients. For instance, both rs309605 and rs309604 can be genotyped in a clinical trial or as a companion diagnostic method, and the name Denovo Genetic Marker 1 (DGM1) can encompass both markers. For example, when a subject is genotyped as AA or AB for both rs309605 and rs309604, the subject is classified as DGM1 positive. Thus, a DGM1-positive subject may include those with the following genotypes: (1) genotype AA at rs309605 and AA at rs309604; (2) genotype AB at rs309605 and AA at rs309604; (3) genotype AA at rs309605 and AB at rs309604; and (4) genotype AB at rs309605 and AB at rs309604. A DGM1-negative subject may include those with the following genotypes: (1) genotype BB at rs309605 and AA at rs309604; (2) genotype BB at rs309605 and AB at rs309604; (3) genotype AA at rs309605 and BB at rs309604; and (4) genotype AB at rs309605 and BB at rs309604.

Using more than one marker (e.g., using both rs309605 and rs309604 in the case of DGM1) in the clinical trial can help identify and minimize the impact of errors, such as the sequencing errors and/or genotyping errors. However, it is not necessary to use more than one marker for the companion diagnostic method disclosed herein. Any one of the markers disclosed herein is sufficient for the method. For example, FIGS. 2-4 show the results observed using rs309605 as the marker independent of other SNPs. Similar results were obtained using rs309604 as the marker independent of other SNPs. Thus, in one embodiment, only rs309605 is used as the companion marker, and a subject genotyped as AA or AB is positive for the marker, while a subject genotyped as BB is negative for the marker. In another embodiment, only rs309604 is used as the companion marker, and a subject genotyped as AA or AB is positive for the marker, while a subject genotyped as BB is negative for the marker.

In addition, exemplary SNPs in linkage disequilibrium with rs309605 in CEU populations are provided in Table 1A. The linkage disequilibrium varies in different ethnic groups, for instance the SNPs in linkage disequilibrium with rs309605 in Chinese are shown in Table 1B. SNPs in linkage disequilibrium with rs309605 in British populations in England and Scotland are provided in Table 1C. SNPs in linkage disequilibrium with rs309605 in Japanese populations in Tokyo are provided in Table 1D. SNPs in linkage disequilibrium with rs309605 in Toscani populations in Italy are provided in Table 1E. SNPs in linkage disequilibrium with rs309605 in Yoruba populations in Ibadan, Nigeria are provided in Table 1F. SNPs in linkage disequilibrium with rs309605 in Mexican Ancestry populations in Los Angeles are provided in Table 1G. SNPs in linkage disequilibrium with rs309605 in Bengali populations in Bangladesh are provided in Table 1H.

Therefore, in one aspect, different SNPs may be used in patients from different ethnic groups to predict enzastaurin activity and/or responsiveness. Additional predicting SNPs might reside on genes related to the genes that markers listed in Tables 1A to 1H and Table 2 are associated with. SNPs that are in linkage disequilibrium may be found in various public databases, e.g., HapMap and 1000 Genome Project. The 1000 Genomes Project resources, including genotypes, sequences, and genome mapping data are available at World Wide Web address 1000genomes.org, or through the NCBI Browser address ncbi.nlm.nih.gov/variation/tools/1000genomes. The HapMap data are available via FTP from ftp.ncbi.nlm nih.gov/hapmap.

In one embodiment, a marker that exhibits correlation with rs309605 is used as the companion marker. In specific embodiments, the $r^2$ value between the marker and rs309605 is equal to or greater than about 0.800, such as equal to or greater than about 0.808, equal to or greater than about 0.809, equal to or greater than about 0.827, equal to or greater than about 0.840, equal to or greater than about 0.850, equal to or greater than about 0.852, equal to or greater than about 0.854, equal to or greater than about 0.874, equal to or greater than about 0.894, equal to or greater than about 0.913, equal to or greater than about 0.915, equal to or greater than about 0957, or equal to or greater than about 0.978, or the $r^2$ value is about 1.000. In specific embodiments, the $r^2$ value between the marker and rs309605 is equal to or greater than about the $r^2$ values listed in any of Tables 1A to 1H.

In one embodiment, a marker that is in linkage disequilibrium with rs309605 is used as the companion marker. In specific embodiments, the D' value of linkage equilibrium of the marker is equal to or greater than about 0.900, such as equal to or greater than about 0.951, equal to or greater than about 0.953, equal to or greater than about 0.954, equal to or greater than about 0.956, or equal to or greater than about 0.973, or the D' value of linkage equilibrium is about 1.000. In specific embodiments, the D' value of linkage equilibrium of the marker is equal to or greater than about the D' values listed in any of Tables 1A to 1H.

In some embodiments, any one of the markers listed in any one of Tables 1A to 1H is used as the companion marker, and a subject genotyped as AA or AB is positive for the marker, while a subject genotyped as BB is negative for the marker. In a specific embodiment, rs5894240 is used as the companion marker, and a subject genotyped as AA or AB is positive for the marker, while a subject genotyped as BB is negative for the marker. In another embodiment, rs1494748 is used as the companion marker, and a subject genotyped as AA or AB is positive for the marker, while a subject genotyped as BB is negative for the marker. In yet another embodiment, rs7836309 is used as the companion marker, and a subject genotyped as AA or AB is positive for the marker, while a subject genotyped as BB is negative for the marker. Any two or more of the markers, from the group consisting of rs309605 and those listed in Tables 1A to 1H, can be used in combination. In one particular example, when a subject is genotyped as AA or AB for all of the two or more SNPs, the subject is classified as positive.

The newly discovered biomarkers and others in linkage disequilibrium with them can be used in companion diagnostic tests which can help to predict drug responses and apply drugs only to those who will be benefited, or exclude those who might have adverse effects, by the treatment.

The frequency report of rs309605 in various populations is shown in Table 2. A population is a group (usually a large group) of individuals. Human population samples corresponds to samples chosen from a population defined by, for example, ethnicity (population of origin) and geography. For example, population sample could be chosen from different ethnic group such as African, African-American, Caucasian, Asian, Asian-American, Chinese, Chinese-American, and also depending on the geography: for example Chinese-American from Hawaii. Alternatively, human population samples can be selected from an experimental population such as individuals in a diseased population or individuals that react in a particular manner when administered a drug and compared to a control population such as healthy individuals.

TABLE 1A

Variants linked to rs309605 in 1000GENOMES:phase_3:CEU

| Variant | Location | Distance (bp) | The correlation between a pair of loci. R2 | D' value of linkage equilibrium |
|---|---|---|---|---|
| rs309604 | 8:115118080 | 965 | 1 | 1 |
| rs5894240 | 8:115118168 | 1053 | 1 | 1 |
| rs1494748 | 8:115120550 | 3435 | 1 | 1 |
| rs7836309 | 8:115141777 | 24662 | 1 | 1 |
| rs309607 | 8:115106460 | 10655 | 0.978 | 1 |
| rs2132025 | 8:115134098 | 16983 | 0.978 | 1 |
| rs11990158 | 8:115138529 | 21414 | 0.978 | 1 |
| rs6469570 | 8:115138537 | 21422 | 0.978 | 1 |
| rs309603 | 8:115110087 | 7028 | 0.957 | 1 |
| rs923967 | 8:115141083 | 23968 | 0.915 | 1 |
| rs1494751 | 8:115102755 | 14360 | 0.913 | 0.956 |
| rs2575943 | 8:115101855 | 15260 | 0.913 | 0.956 |
| rs167446 | 8:115089696 | 27419 | 0.913 | 0.956 |
| rs309606 | 8:115113909 | 3206 | 0.894 | 1 |
| rs72675965 | 8:115135123 | 18008 | 0.894 | 1 |
| rs309602 | 8:115110991 | 6124 | 0.874 | 1 |
| rs309608 | 8:115104783 | 12332 | 0.874 | 1 |
| rs309610 | 8:115104379 | 12736 | 0.874 | 1 |
| rs2575911 | 8:115109205 | 7910 | 0.854 | 1 |
| rs309609 | 8:115104507 | 12608 | 0.854 | 1 |
| rs170132 | 8:115089759 | 27356 | 0.852 | 0.954 |
| rs386413735 | 8:115108280-115108281 | 8835 | 0.85 | 0.953 |
| rs2642789 | 8:115099064 | 18051 | 0.809 | 0.951 |
| rs2642788 | 8:115099063 | 18052 | 0.809 | 0.951 |
| rs2575944 | 8:115098316 | 18799 | 0.809 | 0.951 |
| rs309614 | 8:115094244 | 22871 | 0.809 | 0.951 |
| rs309601 | 8:115112462 | 4653 | 0.808 | 1 |

TABLE 1B

Variants linked to rs309605 in 1000GENOMES:phase_3:CHB, Han Chinese in Beijing, China

| Variant | Location | Distance (bp) | r2 | D' |
|---|---|---|---|---|
| rs309604 | 8:115118080 | 965 | 1.000 | 1.000 |
| rs1494748 | 8:115120550 | 3435 | 1.000 | 1.000 |
| rs2132025 | 8:115134098 | 16983 | 0.840 | 0.973 |
| rs11990158 | 8:115138529 | 21414 | 0.840 | 0.973 |
| rs6469570 | 8:115138537 | 21422 | 0.840 | 0.973 |
| rs7836309 | 8:115141777 | 24662 | 0.840 | 0.973 |
| rs309603 | 8:115110087 | 7028 | 0.827 | 1.000 |
| rs309607 | 8:115106460 | 10655 | 0.827 | 1.000 |
| rs1494751 | 8:115102755 | 14360 | 0.827 | 1.000 |
| rs2575943 | 8:115101855 | 15260 | 0.827 | 1.000 |

TABLE 1C

Variants linked to rs309605 in 1000GENOMES:phase_3:GBR (British in England and Scotland)

| Variant | Location | Distance (bp) | r2 | D' |
|---|---|---|---|---|
| rs309604 | 8:116130309 | 965 | 1 | 1 |
| rs1494748 | 8:116132779 | 3435 | 1 | 1 |
| rs5894240 | 8:116130397 | 1053 | 0.977 | 1 |
| rs309603 | 8:116122316 | 7028 | 0.977 | 1 |
| rs309607 | 8:116118689 | 10655 | 0.977 | 1 |
| rs1494751 | 8:116114984 | 14360 | 0.977 | 1 |
| rs2575943 | 8:116114084 | 15260 | 0.977 | 1 |
| rs167446 | 8:116101925 | 27419 | 0.977 | 1 |
| rs7836309 | 8:116154006 | 24662 | 0.955 | 1 |
| rs2132025 | 8:116146327 | 16983 | 0.954 | 1 |
| rs11990158 | 8:116150758 | 21414 | 0.954 | 1 |
| rs6469570 | 8:116150766 | 21422 | 0.931 | 0.976 |
| rs386413735 | 8:116120509-116120510 | 8835 | 0.889 | 1 |
| rs170132 | 8:116101988 | 27356 | 0.888 | 0.976 |
| rs923967 | 8:116153312 | 23968 | 0.865 | 0.975 |
| rs309601 | 8:116124691 | 4653 | 0.847 | 0.975 |
| rs218361 | 8:116110725 | 18619 | 0.847 | 0.975 |
| rs218362 | 8:116110213 | 19131 | 0.847 | 0.975 |
| rs309616 | 8:116104040 | 25304 | 0.847 | 0.975 |
| rs309618 | 8:116099632 | 29712 | 0.847 | 0.975 |
| rs309606 | 8:116126138 | 3206 | 0.827 | 1 |
| rs2575911 | 8:116121434 | 7910 | 0.827 | 1 |
| rs309608 | 8:116117012 | 12332 | 0.827 | 1 |
| rs309609 | 8:116116736 | 12608 | 0.827 | 1 |
| rs309610 | 8:116116608 | 12736 | 0.827 | 1 |
| rs2642789 | 8:116111293 | 18051 | 0.827 | 1 |
| rs2642788 | 8:116111292 | 18052 | 0.827 | 1 |
| rs2575944 | 8:116110545 | 18799 | 0.827 | 1 |
| rs309614 | 8:116106473 | 22871 | 0.827 | 1 |
| rs309617 | 8:116102742 | 26602 | 0.827 | 1 |
| rs309602 | 8:116123220 | 6124 | 0.807 | 1 |
| rs72675965 | 8:116147352 | 18008 | 0.802 | 0.973 |

TABLE 1D

Variants linked to rs309605 in 1000GENOMES:phase_3:JPT

| Variant | Location | Distance (bp) | r2 | D' |
|---|---|---|---|---|
| rs309604 | 8:116130309 | 965 | 1 | 1 |
| rs1494748 | 8:116132779 | 3435 | 1 | 1 |
| rs6469570 | 8:116150766 | 21422 | 0.827 | 0.945 |
| rs7836309 | 8:116154006 | 24662 | 0.827 | 0.945 |
| rs309607 | 8:116118689 | 10655 | 0.818 | 1 |

TABLE 1E

Variants linked to rs309605 in 1000GENOMES:phase_3:TSI (Toscani in Italy)

| Variant | Location | Distance (bp) | r2 | D' |
|---|---|---|---|---|
| rs309604 | 8:116130309 | 965 | 1 | 1 |
| rs1494748 | 8:116132779 | 3435 | 0.98 | 1 |
| rs5894240 | 8:116130397 | 1053 | 0.98 | 1 |
| rs309607 | 8:116118689 | 10655 | 0.96 | 1 |
| rs309606 | 8:116126138 | 3206 | 0.94 | 1 |
| rs7836309 | 8:116154006 | 24662 | 0.939 | 0.979 |
| rs923967 | 8:116153312 | 23968 | 0.919 | 0.959 |
| rs309603 | 8:116122316 | 7028 | 0.901 | 1 |
| rs309608 | 8:116117012 | 12332 | 0.901 | 1 |
| rs309602 | 8:116123220 | 6124 | 0.882 | 1 |
| rs2575911 | 8:116121434 | 7910 | 0.882 | 1 |
| rs309609 | 8:116116736 | 12608 | 0.882 | 1 |
| rs309610 | 8:116116608 | 12736 | 0.882 | 1 |
| rs1494751 | 8:116114984 | 14360 | 0.88 | 0.978 |
| rs2575943 | 8:116114084 | 15260 | 0.88 | 0.978 |
| rs167446 | 8:116101925 | 27419 | 0.88 | 0.978 |
| rs11990158 | 8:116150758 | 21414 | 0.879 | 0.957 |
| rs6469570 | 8:116150766 | 21422 | 0.879 | 0.957 |
| rs2132025 | 8:116146327 | 16983 | 0.863 | 1 |
| rs2642789 | 8:116111293 | 18051 | 0.861 | 0.977 |
| rs2642788 | 8:116111292 | 18052 | 0.861 | 0.977 |
| rs2575944 | 8:116110545 | 18799 | 0.861 | 0.977 |
| rs309614 | 8:116106473 | 22871 | 0.861 | 0.977 |
| rs309617 | 8:116102742 | 26602 | 0.861 | 0.977 |
| rs72675965 | 8:116147352 | 18008 | 0.845 | 1 |
| rs386413735 | 8:116120509-116120510 | 8835 | 0.84 | 0.955 |
| rs79927251 | 8:116098007-116098008 | 31337 | 0.84 | 0.955 |

TABLE 1F

Variants linked to rs309605 in 1000GENOMES:phase_3:YRI (Yoruba in Ibadan, Nigeria)

| Variant | Location | Distance (bp) | r2 | D' |
|---|---|---|---|---|
| rs309604 | 8:116130309 | 965 | 1 | 1 |
| rs1494748 | 8:116132779 | 3435 | 0.98 | 1 |

TABLE 1G

Variants linked to rs309605 in 1000GENOMES:phase_3:MXL (Mexican Ancestry in Los Angeles)

| Variant | Location | Distance (bp) | r2 | D' |
|---|---|---|---|---|
| rs309604 | 8:116130309 | 965 | 1 | 1 |
| rs1494748 | 8:116132779 | 3435 | 1 | 1 |
| rs2132025 | 8:116146327 | 16983 | 0.965 | 1 |
| rs11990158 | 8:116150758 | 21414 | 0.965 | 1 |
| rs6469570 | 8:116150766 | 21422 | 0.965 | 1 |
| rs7836309 | 8:116154006 | 24662 | 0.965 | 1 |
| rs309607 | 8:116118689 | 10655 | 0.964 | 1 |
| rs309603 | 8:116122316 | 7028 | 0.929 | 1 |
| rs1494751 | 8:116114984 | 14360 | 0.929 | 1 |
| rs2575943 | 8:116114084 | 15260 | 0.929 | 1 |
| rs167446 | 8:116101925 | 27419 | 0.929 | 1 |
| rs170132 | 8:116101988 | 27356 | 0.892 | 0.962 |

TABLE 1H

Variants linked to rs309605 in 1000GENOMES:phase_3:BEB (Bengali in Bangladesh)

| Variant | Location | Distance (bp) | r2 | D' |
|---|---|---|---|---|
| rs309604 | 8:116130309 | 965 | 1 | 1 |
| rs1494748 | 8:116132779 | 3435 | 1 | 1 |
| rs309607 | 8:116118689 | 10655 | 0.977 | 1 |
| rs1494751 | 8:116114984 | 14360 | 0.977 | 1 |
| rs2575943 | 8:116114084 | 15260 | 0.977 | 1 |
| rs170132 | 8:116101988 | 27356 | 0.977 | 1 |
| rs167446 | 8:116101925 | 27419 | 0.977 | 1 |
| rs2132025 | 8:116146327 | 16983 | 0.907 | 0.953 |
| rs11990158 | 8:116150758 | 21414 | 0.907 | 0.953 |
| rs6469570 | 8:116150766 | 21422 | 0.907 | 0.953 |
| rs5894240 | 8:116130397 | 1053 | 0.868 | 1 |
| rs7836309 | 8:116154006 | 24662 | 0.863 | 0.951 |

TABLE 2

SNP info: refSNP rs309605 with alleles A/G in dbSNP b126 (dbSNP report | Ensembl SNPview)
Genomic location: chr8: 116198520..116198520. (−) strand relative to the human reference sequence
Frequency report

| Population | Genotype frequencies | | | | | | | | | Allele frequencies | | | | | | |
|---|---|---|---|---|---|---|---|---|---|---|---|---|---|---|---|---|
| | | | | | | | | | | Ref-allele | | | Other-allele | | | |
| | genotype | freq | count | genotype | freq | count | genotype | freq | count | Total | allele | freq | count | allele | freq | count | Total | |
| ASW (A) | C/C | 0.321 | 17 | C/T | 0.415 | 22 | T/T | 0.264 | 14 | 53 | C | 0.528 | 56 | T | 0.472 | 60 | 106 | retrieve genotypes |
| CEU (C) | C/C | 0.116 | 13 | C/T | 0.491 | 55 | T/T | 0.393 | 44 | 112 | C | 0.362 | 81 | T | 0.638 | 143 | 224 | retrieve genotypes |
| CHB (H) | C/C | 0.048 | 4 | C/T | 0.440 | 37 | T/T | 0.512 | 43 | 84 | C | 0.268 | 45 | T | 0.732 | 123 | 168 | retrieve genotypes |

TABLE 2-continued

SNP info: refSNP rs309605 with alleles A/G in dbSNP b126 (dbSNP report | Ensembl SNPview)
Genomic location: chrS: 116198520..116198520. (−) strand relative to the human reference sequence
Frequency report

| Population | Genotype frequencies | | | | | | | | | Allele frequencies | | | | | | |
|---|---|---|---|---|---|---|---|---|---|---|---|---|---|---|---|---|
| | | | | | | | | | | Ref-allele | | | Other-allele | | | |
| | genotype | freq | count | genotype | freq | count | genotype | freq | count | Total | allele | freq | count | allele | freq | count | Total |
| CHD (D) | C/C | 0.047 | 4 | C/T | 0.353 | 30 | T/T | 0.600 | 51 | 85 | C | 0.224 | 38 | T | 0.776 | 132 | 170 retrieve genotypes |
| GIH (G) | C/C | 0.261 | 23 | C/T | 0.420 | 37 | T/T | 0.318 | 28 | 88 | C | 0.472 | 83 | T | 0.528 | 93 | 176 retrieve genotypes |
| JPT (J) | C/C | 0.058 | 5 | C/T | 0.349 | 30 | T/T | 0.593 | 51 | 86 | C | 0.233 | 40 | T | 0.767 | 132 | 172 retrieve genotypes |
| LWK (L) | C/C | 0.333 | 30 | C/T | 0.522 | 47 | T/T | 0.144 | 13 | 90 | C | 0.594 | 107 | T | 0.406 | 73 | 180 retrieve genotypes |
| MEX (M) | C/C | 0.040 | 2 | C/T | 0.540 | 27 | T/T | 0.420 | 21 | 50 | C | 0.310 | 31 | T | 0.690 | 69 | 100 retrieve genotypes |
| MKK (M) | C/C | 0.280 | 40 | C/T | 0.517 | 74 | T/T | 0.203 | 29 | 143 | C | 0.538 | 154 | T | 0.462 | 132 | 286 retrieve genotypes |
| TSI (T) | C/C | 0.102 | 9 | C/T | 0.489 | 43 | T/T | 0.409 | 36 | 88 | C | 0.347 | 61 | T | 0.653 | 115 | 176 retrieve genotypes |
| YRI (T) | C/C | 0.363 | 41 | C/T | 0.513 | 58 | T/T | 0.124 | 14 | 113 | C | 0.619 | 140 | T | 0.381 | 86 | 226 retrieve genotypes |

Note:
the 'reference' allele as the base observed in the reference genome sequence at this location
Populaton descriptors:
ASW (A): African ancestry in Southwest USA
CEU (C): Utah residents with Northern and Western European ancestry from CEPH collection
CHB (H): Han Chinese in Beijing, China
CHD (D): Chinese in Metropolitan Denver, Colorado
GIH (G): Gujarati Indians in Houston, Texas.
JPT (J): Japanese in Tokyo, Japan
LWK (L): Luhya in Webuye, Kenya
MEX (M): Mexican ancestry in Los Angeles, California
MKK (K): Mansai in Kinyawa, Kenya
TSI (T): Tuscan in Italy

TABLE 3

Chromaturia vs Non-chromaturial in Enza-treated patients, potential synergistic effects with Gtype AA + AB (rs309605) in overall survival (OS)

| | AA + AB | | All types (AA, AB, BB) | |
|---|---|---|---|---|
| | Chrom | Non-Chrom | Chrom | Non-Chrom |
| N | 82 | 158 | 95 | 187 |
| Number of events | 3 | 27 | 10 | 41 |
| Total person-month | 4593.7 | 7324.2 | 5094.5 | 8492.4 |
| Event per 1000 person-month | 0.65 | 3.69 | 1.96 | 4.83 |
| Hazard ratio (95% CI) relative to Chrom, Cox regression | 0.18 (0.05, 0.59) | | 0.41 (0.20, 0.81) | |

P = 0.017 for chromaturia subgroup and gtype interaction, Cox regression

With the increasing number of single nucleotide polymorphisms, such as those identified by the SNP Consortium and the novel methods of genotyping, association studies between DNA variants and disease will increase. Because of the limitations of other linkage methodologies, linkage disequilibrium mapping has become the strategy of choice to map complex diseases through the whole genome.

In one aspect, LD refers to a population association among alleles at two or more loci. It is a measure of co-segregation of alleles in a population. Linkage disequilibrium or allelic association is the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

A marker in linkage disequilibrium can be particularly useful in detecting susceptibility to disease (or other phenotype). The marker may or may not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable. In one aspect, the term allele frequency corresponds to the fraction of the number of individuals with a given allele over the total number of alleles in the population tested.

In some embodiments, linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium." In contrast, LD refers to any non-random genetic association between allele(s) at two or more different SNP sites, which is generally due to the physical proximity of the two loci along a chromosome. See e.g., U.S. 2008/0299125, which is incorporated herein by reference.

Linkage disequilibrium is influenced by many factors, including selection, the rate of recombination, the rate of mutation, genetic drift, the system of mating, population structure, and genetic linkage, etc. As a result, the pattern of linkage disequilibrium in a genome is a powerful signal of the population genetic processes that are structuring it. In spite of its name, linkage disequilibrium may exist between alleles at different loci without any genetic linkage between them and independently of whether or not allele frequencies are in equilibrium (not changing with time). Suppose that among the gametes that are formed in a sexually reproducing population, allele A occurs with frequency $p_A$ at one locus (i.e. $p_A$ is the proportion of gametes with A at that locus), while at a different locus allele B occurs with frequency $p_B$. Similarly, let $p_{AB}$ be the frequency with which both A and B occur together in the same gamete (i.e. $p_{AB}$ is the frequency of the AB haplotype). The association between the alleles A and B can be regarded as completely random when the occurrence of one does not affect the occurrence of the other, in which case the probability that both A and B occur together is given by the product $P_A \times p_B$ of the probabilities. A linkage disequilibrium between the two alleles exists whenever $p_{AB}$ differs from $p_A \times p_B$ for any reason.

The level of linkage disequilibrium between A and B can be quantified by the coefficient of linkage disequilibrium $D_{AB}$, which is defined as $D_{AB}=p_{AB}-p_A \times p_B$, provided that both $p_A$ and $p_B$ are greater than zero. The coefficient of linkage disequilibrium $D_{AB}$ is not always a convenient measure of linkage disequilibrium because its range of possible values depends on the frequencies of the alleles it refers to. $D_{AB}$ may be normalized by dividing it by the theoretical maximum difference between the observed and expected allele frequencies, to calculate the D' value:

$$D'_{AB} = \begin{cases} \dfrac{D_{AB}}{\min(p_A p_B, p_a p_b)} & D_{AB} < 0 \\ \dfrac{D_{AB}}{\min(p_A p_b, p_a p_B)} & D_{AB} > 0 \end{cases}.$$

An alternative to the D' value is the correlation coefficient between pairs of loci, expressed as:

$$\Delta^2 = \frac{D_{AB}^2}{p_A(1-p_A)p_B(1-p_B)}$$
$$= \frac{\chi^2}{2n}.$$

In some embodiments, LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD. See e.g., U.S. 2008/0299125, which is incorporated herein by reference.

In some embodiments, for diagnostic and/or companion diagnostic purposes, if a particular SNP site is found to be useful for diagnosis and/or companion diagnosis, then the skilled artisan would recognize that other SNP sites which are in LD with this SNP site would also be useful for diagnosis and/or companion diagnosis of the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome. See e.g., U.S. 2008/0299125, which is incorporated herein by reference.

Methods of analysis of LD and/or identifying loci that are in LD with a known locus are known in the art, for example, as disclosed in U.S. 2004/0072217. Examples of software for analyzing and/or simulating LD include PLINK (zzz.bwh.harvard.edu/plink), LDHat (ldhat.sourceforge.net), Haploview (www.broadinstitute.org/haploview/haploview), LdCompare (see e.g., Hao et al., LdCompare: rapid computation of single- and multiple-marker r2 and genetic coverage, *Bioinformatics* 2007, 23(2):252-4), SNP and Variation Suite (goldenhelix.com/products/SNP_Variation/index.html), GOLD (csg.sph.umich.edu/abecasis/GOLD/index.html), TASSEL (www.maizegenetics.net/tassel), rAggr (raggr.usc.edu), SNeP (sourceforge.net/projects/snepnetrends), and Haploid (haploid.nongnu.org), all of which are incorporated herein by reference.

D. Applications of the Biomarkers

Information generated from genomic biomarkers described herein can be used to determine appropriate dosage and/or treatment regimens for an individual with cancers such as GBM and DLBCL. This knowledge, when applied to dosing or drug selection, can avoid adverse reactions or therapeutic failure and thus enhance therapeutic efficiency when administering a therapeutic composition, such as enzastaurin.

The biomarkers disclosed herein and their associated SNPs or genes could also be used to predict patient's responses to treatment of other diseases or conditions besides GBM and DLBCL. These diseases include, but are not limited to, lymphoma, lung cancer, prostate cancer, breast cancer, cancer prevention.

Pharmacogenomics involves tailoring a treatment for a subject according to the subject's genotype as a particular treatment regimen may exert a differential effect depending upon the subject's genotype. For example, based upon the outcome of a prognostic test, a clinician or physician may target pertinent information and preventative or therapeutic treatments to a subject who would be benefited by the information or treatment and avoid directing such information and treatments to a subject who would not be benefited (e.g., the treatment has no therapeutic effect and/or the subject experiences adverse side effects). Information generated from pharmacogenomic biomarkers using a method described herein can be used to determine appropriate dosage and treatment regimens for an individual. This knowledge, when applied to dosing or drug selection, can avoid adverse reactions or therapeutic failure and thus enhance therapeutic efficiency when administering a therapeutic composition. In some embodiments, the pharmacogenomic biomarker may be used to develop a companion diagnostic test.

Therefore, in a further aspect, provided herein is a companion diagnostic test using the biomarkers disclosed herein. For example, in one embodiment, a physician or clinician may consider applying knowledge obtained in biomarkers using a method described herein, when determining whether to administer a pharmaceutical composition to a subject. In another embodiment, a physician or clinician may consider applying such knowledge when determining the dosage, e.g., amount per treatment or frequency of treatments, of a treatment, administered to a patient.

The invention provides methods for assessing or aiding assessment of responsiveness of a subject to treatment. The invention also provides methods for predicting responsiveness or monitoring treatment/responsiveness to a treatment in a subject. The invention provides methods for selecting a subject for treatment and treating the subject. In some embodiments, the methods comprise assessing one or more pharmacogenomic biomarkers in a sample obtained from the subject; and predicting, assessing, or aiding assessment of responsiveness of the subject to a treatment based on the genotype of said one or more pharmacogenomic biomarkers. In some embodiments, the responsiveness is predicted or assessed by classifying the subject using an algorithm such as support vector machine (SVM), logistic regression, or K-nearest neighbors analysis.

The following is an example of a pharmacogenomic embodiment. A particular treatment regimen can exert a differential effect depending upon the subject's genotype, for example, at one or both alleles. Where a candidate therapeutic exhibits a significant interaction with a major allele and a comparatively weak interaction with a minor allele (e.g., an order of magnitude or greater difference in the interaction), such a therapeutic typically would not be administered to a subject genotyped as being homozygous for the minor allele, and sometimes not administered to a subject genotyped as being heterozygous for the minor allele. For example, when a therapeutic effect of an agent is associated with a major allele (e.g., allele A) and not with a minor allele (e.g., allele B), or more strongly associated with the major allele than with the minor allele, such a therapeutic agent typically would be administered to a subject genotyped as being homozygous or heterozygous for the major allele (AA or AB) and would not be administered to a subject genotyped as being homozygous for the minor allele (BB). In another example, when a therapeutic effect of an agent is associated with a major allele (e.g., allele A) and not with a minor allele (e.g., allele B), or more strongly associated with the major allele than with the minor allele, such a therapeutic agent can be administered to a subject genotyped as being homozygous (AA) for the major allele, but not to a subject genotyped as being heterozygous or homozygous for the minor allele (AB or BB). In yet another example, a therapeutic effect of an agent can be associated with a genotype (AA, AB, or BB) rather than the presence of a major or minor allele. For instance, the therapeutic effect may be associated with the genotype AA, AB, and BB with varying degrees, and subjects of the three different genotypes may be treated with the agent at varying doses and/or for varying duration.

or adverse effect (such as toxicity)

In another example, where a candidate therapeutic is not significantly toxic when administered to subjects who are homozygous for a major allele but is comparatively toxic when administered to subjects heterozygous or homozygous for a minor allele, the candidate therapeutic is not typically administered to subjects who are genotyped as being heterozygous or homozygous with respect to the minor allele.

The methods described herein are applicable to pharmacogenomic methods for preventing, alleviating or treating conditions such as metabolic disorders, cardiovascular diseases, cancers, etc. For example, a nucleic acid sample from an individual may be subjected to a prognostic test described herein. Where one or more polymorphic variations associated with increased risk of a condition, disorder, or disease, such as a cancer, are identified in a subject, information for preventing or treating the condition, disorder, or disease and/or information about the safety and/or efficacy of one or more treatment regimens for the condition, disorder, or disease then may be prescribed to that subject.

In certain embodiments, a treatment regimen is specifically prescribed and/or administered to individuals who will most benefit from it based upon their likelihood of responding to a treatment regimen assessed by the methods described herein. Thus, provided are methods for identifying a subject with a high likelihood of responding to a treatment regimen and then prescribing such treatment regimen to individuals identified as having a high likelihood of responding. Thus, certain embodiments are directed to a method for treating a subject, which comprises: detecting the presence or absence of a pharmacogenomic biomarker associated with responsiveness to a treatment regimen in a nucleotide sequence set forth herein in a nucleic acid sample from a subject, and prescribing or administering the treatment regimen to a subject from whom the sample originated where the presence of a pharmacogenomic biomarker associated with responsiveness to the treatment regimen is detected in the nucleotide sequence.

The treatment sometimes is preventative (e.g., is prescribed or administered to reduce the probability that a disease condition arises or progresses), sometimes is therapeutic, and sometimes delays, alleviates or halts the progression of a disease condition. Any known preventative or therapeutic treatment for alleviating or preventing the occurrence of a disorder may be prescribed and/or administered.

Pharmacogenomics methods also may be used to analyze and predict a response to a drug. For example, if pharmacogenomics analysis indicates a likelihood that an individual will respond positively to a treatment with a particular drug, the drug may be administered to the individual. Conversely, if the analysis indicates that an individual is likely to respond negatively to treatment with a particular drug, an alternative course of treatment may be prescribed. The response to a therapeutic treatment can be predicted in a background study in which subjects in any of the following populations are genotyped: a population that responds favorably to a treatment regimen, a population that does not respond significantly to a treatment regimen, and a population that responds adversely to a treatment regiment (e.g., exhibits one or more side effects). These populations are provided as examples and other populations and subpopulations may be analyzed. Based upon the results of these analyses, a subject is genotyped to predict whether he or she will respond favorably to a treatment regimen, not respond significantly to a treatment regimen, or respond adversely to a treatment regimen.

A classification/prediction algorithm may be developed using the verification and/or replication dataset. An imputation algorithm that can replace some of the missing data based on LD among the genotyped polymorphic loci may be used. In embodiments where SNPs are used for genotyping, SNP databases such as Hapmap may be used for the imputation algorithm. For development of the classification/prediction algorithm, the verification dataset may be used as a training dataset. Once a classification/prediction algorithm has been developed, the replication dataset may be used for testing the algorithm.

In some embodiments, the methods of the invention comprise classifying the subject as a responsive or non-responsive subject using a K-nearest neighbors analysis based on the genotype of the pharmacogenomic biomarkers in the sample from the subject and reference samples with known classes. In some embodiments, classifying the subject using a K-nearest neighbors analysis is carried out by (1) determining parameter K (i.e., number of nearest neighbors); (2) calculating the difference between the measured expression level of the marker genes in the new sample to be classified and the expression level of the respective marker genes in each reference sample; (3) determining the nearest reference samples by selecting those samples with the smallest weighted average of the absolute differences (WARD) between the new sample and the reference sample; and (4) determining class of the new sample based on the known classes of the K nearest reference samples. The weights and/or parameter K are determined using cross-validation with clinical trial samples with known classes. For example, 5-fold (such as 5-fold, 6-fold, 7-fold, 8-fold, 9-fold, or 10-fold) to N-fold cross-validation may be used to minimize the weighted K-nearest neighbors classification error, wherein N is the size of the samples. In some embodiments, K is an integer between 4 and 13 (e.g., 4, 5, 6, 7, 8, 9, 10, 11, 12, and 13). In some embodiments, the nearest reference samples (nearest neighbors) are those with the smallest weighted average of the absolute differences between the expression level of the new sample to be classified and the expression level of each reference sample for each of the pharmacogenomic biomarkers.

The comparisons and/or calculations for predicting, assessing or aiding assessment can be carried out in any convenient manner appropriate to the type of measured value and/or reference value for the pharmacogenomic biomarkers at issue. The process of comparing or calculating may be manual or it may be automatic (such as by a machine including computer-based machine). As will be apparent to those of skill in the art, replicate genotyping may be taken for the pharmacogenomic biomarkers.

Also provided herein is a method of prognosticating responsiveness of a subject to a treatment using the companion diagnostic test disclosed herein. The tests described herein also are applicable to clinical drug trials. In some embodiments, the pharmacogenomic biomarkers can be used to stratify or select a subject population for a clinical trial. The pharmacogenomic biomarkers can, in some embodiments, be used to stratify individuals that may exhibit a toxic response to a treatment from those that will not. In other embodiments, the pharmacogenomic biomarkers can be used to separate those that will be non-responders from those who will be responders. The pharmacogenomic biomarkers described herein can be used in pharmacogenomic-based design and in managing the conduct of a clinical trial.

One or more pharmacogenomic biomarkers indicative of response to a therapeutic agent or side effects to a therapeutic agent may be identified. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Thus, another embodiment is a method of selecting an individual for inclusion in a clinical trial of a treatment or drug comprising the steps of: (a) obtaining a nucleic acid sample from an individual; (b) determining the identity of a polymorphic variation which is associated with a positive response to the treatment or the drug, or at least one polymorphic variation which is associated with a negative response to the treatment or the drug in the nucleic acid sample, and (c) including the individual in the clinical trial if the nucleic acid sample contains said polymorphic variation associated with a positive response to the treatment or the drug or if the nucleic acid sample lacks said polymorphic variation associated with a negative response to the treatment or the drug. In addition, the methods described herein for selecting an individual for inclusion in a clinical trial of a treatment or drug encompass methods with any further limitation described in this disclosure, or those following, specified alone or in any combination. The including step (c) optionally comprises administering the drug or the treatment to the individual if the nucleic acid sample contains the polymorphic variation associated with a positive response to the treatment or the drug and the nucleic acid sample lacks said biallelic marker associated with a negative response to the treatment or the drug.

E. Additional Biomarkers or Drug Targets

Also provided herein is a method for identifying polymorphic variants proximal to the biomarkers disclosed herein. In some embodiments, the proximal polymorphic variant identified sometimes is a publicly disclosed polymorphic variant, which for example, sometimes is published in a publicly available database. In other embodiments, the polymorphic variant identified is not publicly disclosed and is discovered using a known method, including, but not limited to, sequencing a region surrounding the identified pharmacogenomic biomarker in a group of nucleic samples. Thus, multiple polymorphic variants proximal to a biomarker are identified using this method.

The proximal polymorphic variant often is identified in a region surrounding the biomarker. In certain embodiments, this surrounding region is about 50 kb flanking the biomarker (e.g., about 50 kb 5' of the first polymorphic variant and about 50 kb 3' of the first polymorphic variant), and the region sometimes is composed of shorter flanking sequences, such as flanking sequences of about 40 kb, about 30 kb, about 25 kb, about 20 kb, about 15 kb, about 10 kb, about 7 kb, about 5 kb, or about 2 kb 5' and 3' of the biomarker. In other embodiments, the region comprises longer flanking sequences, such as flanking sequences of about 75 kb, about 150 kb, about 300 kb, about 600 kb, about 1,200 kb, about 2,000 kb, about 4,000 kb, about, or about 10,000 kb 5' and 3' of the biomarker.

In certain embodiments, polymorphic variants are identified iteratively. For example, a first proximal polymorphic variant is identified using the methods described above and then another polymorphic variant proximal to the first proximal polymorphic variant is identified (e.g., publicly disclosed or discovered) and the presence or absence of an association of one or more other polymorphic variants proximal to the first proximal polymorphic variant is determined.

The methods described herein are useful for identifying or discovering additional polymorphic variants that may be used to further characterize a gene, region or loci associated with a condition, a disease, or a disorder. For example, allelotyping or genotyping data from the additional polymorphic variants may be used to identify a functional mutation or a region of linkage disequilibrium. In certain embodiments, polymorphic variants identified or discovered within a region comprising the biomarker are genotyped, and it can be determined whether those polymorphic variants are in linkage disequilibrium with the biomarker. The size of the region in linkage disequilibrium with the biomarker also can be assessed using these genotyping methods. Thus, provided herein are methods for determining whether a polymorphic variant is in linkage disequilibrium with a biomarker, and such information can be used in prognosis/diagnosis methods described herein.

Additionally, genes may be identified that are in proximity to the biomarkers, and their functions analyzed. Genes with functions that are directly or indirectly related to the relevant phenotype, or other genes in the same cellular pathway, may be targets for further analysis with the relevant phenotype, and new biomarkers may be identified.

Further provided herein is a method of developing novel therapeutic agents and/or identifying a novel drug target using the biomarkers disclosed herein. In some embodiments, the biomarkers and their associated SNPs or genes could gain insight of the underlying biological pathways or mechanisms underlying the studied phenotypes, such as efficacy, adverse effect, or other endpoints.

F. Reagents and Kits

The present invention contemplates the preparation of kits, chips, devices, or assays for use in accordance with the present invention. Such an assay, chip, device, or a kit may comprise a plurality of primers or probes to detect genetic signature of SNPs such as rs309605 and the ones listed in Tables 1A to 1H and Table 2. Such methods can include instruments and instructions that a subject can use to obtain a sample, e.g., of buccal cells or blood, without the aid of a health care provider.

The invention also contemplates the development of computer algorithm which will convert the test results generated from the measurement of the genomic biomarkers into a score, which will be used to determine in whether an individual should receive the therapeutic invention, such as enzastaurin treatment.

Diagnostic kits based on the biomarkers described above might be developed, and they can be used to predict individual's response to the corresponding drug. Such test kits can include devices and instructions that a subject can use to obtain a sample, e.g., of buccal cells or blood, without the aid of a health care provider.

For use in the applications described or suggested above, kits or articles of manufacture are also provided by the invention. Such kits may comprise at least one reagent specific for genotyping a biomarker described herein, and may further include instructions for carrying out a method described herein.

In some embodiments, the invention provides compositions and kits comprising primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides in a sample and as a means for detecting cell expressing proteins encoded by the polynucleotides. As will be understood by the skilled artisan, a great many different primers and probes may be prepared based on the sequences provided herein and used effectively to amplify, clone and/or determine the presence and/or levels of genomic DNAs.

In some embodiments, the kit may comprise reagents for detecting presence of polypeptides. Such reagents may be antibodies or other binding molecules that specifically bind to a polypeptide. In some embodiments, such antibodies or binding molecules may be capable of distinguishing a structural variation to the polypeptide as a result of polymorphism, and thus may be used for genotyping. The antibodies or binding molecules may be labeled with a detectable marker, such as, for example, a radioisotope, fluorescent compound, bioluminescent compound, a chemiluminescent compound, metal chelator or enzyme. Other reagents for performing binding assays, such as ELISA, may be included in the kit.

In some embodiments, the kits comprise reagents for genotyping at least two, at least three, at least five, at least ten, or more biomarkers. In some embodiments, the kits may further comprise a surface or substrate (such as a microarray) for capture probes for detecting of amplified nucleic acids.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a biomarker. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kit can further comprise a set of instructions and materials for preparing a tissue or cell sample and preparing nucleic acids (such as genomic DNA) from the sample.

The invention provides a variety of compositions suitable for use in performing methods of the invention, which may be used in kits. For example, the invention provides surfaces, such as arrays that can be used in such methods. In some embodiments, an array of the invention comprises individual or collections of nucleic acid molecules useful for detecting pharmacogenomic biomarkers of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of genotypes of the pharmacogenomic biomarkers of the invention.

Several techniques are well known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silica surface chemistry are also known in the art, as disclosed at world wide web at cmt-.corning.com and cmgm.stanford.edu/pbrown1.

Attachment of groups to oligonucleotides which could be later converted to reactive groups is also possible using methods known in the art. Any attachment to nucleotides of oligonucleotides will become part of oligonucleotide, which could then be attached to the solid surface of the microarray Amplified nucleic acids can be further modified, such as through cleavage into fragments or by attachment of detectable labels, prior to or following attachment to the solid substrate, as required and/or permitted by the techniques used.

The invention claimed is:

1. A method of selecting and treating a subject that has diffuse large B-cell lymphoma (DLBCL) or glioblastoma (GBM) and is considered for treatment with enzastaurin, comprising:
   a) obtaining a biological sample from said subject that has DLBCL or GBM and is considered for treatment with enzastaurin;
   b) optionally isolating genomic DNA from said biological sample;
   c) assaying the biological sample for the presence of both single nucleotide polymorphisms (SNPs) rs309605 and rs309604, or complementary SNPs thereof;
   d) identifying a subject assayed to be homozygous or heterozygous for thymidine at both SNPs rs309605 and rs309604, or for deoxyadenosine at complementary strand of both SNPs rs309605 and rs309604, to be a selected subject; and,
   e) administering an effective amount of enzastaurin to said selected subject.

2. A method of selecting and treating a population of subjects that has diffuse large B-cell lymphoma (DLBCL) or glioblastoma (GBM) and each is considered for treatment with enzastaurin, comprising:
   a) obtaining a biological sample from each subject of said population of subjects that has DLBCL or GBM and is being considered for treatment with enzastaurin;
   b) optionally isolating genomic DNA from each of said biological samples;
   c) assaying each of said biological samples for the presence of both single nucleotide polymorphisms (SNPs) rs309605 and rs309604, or complementary SNPs thereof,
   d) identifying subjects of said population assayed to be homozygous or heterozygous for thymidine at both SNPs rs309605 and rs309604, or for deoxyadenosine at complementary strand of both SNPs rs309605 and rs309604, to be selected subjects; and,
   e) administering an effective amount of enzastaurin to each of said selected subjects.

3. The method of claim 1, wherein the treatment further comprises therapy with rituximab-cyclophosphamide, doxorubicin, vincristine, and prednisone (R-CHOP).

4. The method of claim 1, wherein said subject is assayed to be homozygous for thymidine at both SNPs rs309605 and rs309604.

5. The method of claim 1, wherein said subject is assayed to be heterozygous for thymidine at both SNPs rs309605 and rs309604.

6. The method of claim 1, wherein said subject is assayed to be homozygous for thymidine at SNP rs309605 and heterozygous for thymidine at SNP rs309604.

7. The method of claim 1, wherein said subject is assayed to be homozygous for thymidine at SNP rs309604 and heterozygous for thymidine at SNP rs309605.

8. The method of claim 3, wherein said subject is assayed to be homozygous for thymidine at both SNPs rs309605 and rs309604.

9. The method of claim 3, wherein said subject is assayed to be heterozygous for thymidine at both SNPs rs309605 and rs309604.

10. The method of claim 3, wherein said subject is assayed to be homozygous for thymidine at SNP rs309605 and heterozygous for thymidine at SNP rs309604.

11. The method of claim 3, wherein said subject is assayed to be homozygous for thymidine at SNP rs309604 and heterozygous for thymidine at SNP rs309605.

12. The method of claim 2, wherein the treatment further comprises therapy with rituximab-cyclophosphamide, doxorubicin, vincristine, and prednisone (R-CHOP).

13. The method of claim 2, wherein at least one subject of said population is assayed to be homozygous for thymidine at both SNPs rs309605 and rs309604.

14. The method of claim 2, wherein at least one subject of said population is assayed to be heterozygous for thymidine at both SNPs rs309605 and rs309604.

15. The method of claim 2, wherein at least one subject of said population is assayed to be homozygous for thymidine at SNP rs309605 and heterozygous for thymidine at SNP rs309604.

16. The method of claim 2, wherein at least one subject of said population is assayed to be homozygous for thymidine at SNP rs309604 and heterozygous for thymidine at SNP rs309605.

17. The method of claim 12, wherein at least one subject of said population is assayed to be homozygous for thymidine at both SNPs rs309605 and rs309604.

18. The method of claim 12, wherein at least one subject of said population is assayed to be heterozygous for thymidine at both SNPs rs309605 and rs309604.

19. The method of claim 12, wherein at least one subject of said population is assayed to be homozygous for thymidine at SNP rs309605 and heterozygous for thymidine at SNP rs309604.

20. The method of claim 12, wherein at least one subject of said population is assayed to be homozygous for thymidine at SNP rs309604 and heterozygous for thymidine at SNP rs309605.

* * * * *

SEQUENCE LISTING

```
<160> NUMBER OF SEQ ID NOS: 28

<210> SEQ ID NO 1
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 1
tggggaatgt cattccatgt taggcntcat gttgaaacat attatttcat a         51

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 2
gaaggaacac tttccctaat gcccangaag gaacaaggat tctgatagct t         51

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = null or a

<400> SEQUENCE: 3
aaaagcaaaa aaaaaataaa aaaatnaaaa aaaaaaggca aagagacaga a         51

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = g or t

<400> SEQUENCE: 4
cacccgttaa aaaaaaaaaa aaatcngtca ctaattgttc cggttactat t         51

<210> SEQ ID NO 5
<211> LENGTH: 51
<212> TYPE: DNA
<213> ORGANISM: Homo sapiens
<220> FEATURE:
```

<221> NAME/KEY: misc_feature
<222> LOCATION: 26
<223> OTHER INFORMATION: n = g or t

<400> SEQUENCE: 5
atagcaatag gcaacaaaca aactancaaa tatagtgtca agtaccaaaa g    51

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 6
cattctcatc atagtctgct tctcanttga ttcagtattg gatgaagatc a    51

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 7
gctctatttt ataaaagtct attaanttta actgaaatca aaataactac a    51

<210> SEQ ID NO 8
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = g or t

<400> SEQUENCE: 8
tgaatttcat ccaaagcctt ttctgnatct atttagataa taatgtggtt t    51

<210> SEQ ID NO 9
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = g or t

<400> SEQUENCE: 9
atccaaagcc ttttctggat ctattnagat aataatgtgg ttttgtctt t    51

<210> SEQ ID NO 10
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or c

<400> SEQUENCE: 10
ctacagacca agtgaacaac agaggnctgc tgaattcatt cattgcattt t    51

```
<210> SEQ ID NO 11
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or t

<400> SEQUENCE: 11
aacttggggc actctgcact actgcntgcc agcattttaa aaagtcatca g          51

<210> SEQ ID NO 12
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 12
catacaccaa gagttttata aataanttta tttcaatatg aaggttaaat t          51

<210> SEQ ID NO 13
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or t

<400> SEQUENCE: 13
ttaatcggaa tgctccctgc tcctcnctttt attccctaga taaacgtaca c          51

<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 14
atatcattta cattagcaac ctctanaata aaatatttag gtattagcct a          51

<210> SEQ ID NO 15
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 15
ctattatttt cagaacattg cttaanatgt tggttgagtc cggcagacaa a          51

<210> SEQ ID NO 16
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t
```

<400> SEQUENCE: 16
tttattgaaa tacttaaatt tactantgta aatactttta tacttttata t         51

<210> SEQ ID NO 17
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 17
gacctaggag ctccccaagc cagggntgtg acaccgtctt tggggatctc t         51

<210> SEQ ID NO 18
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 18
tccatttaaa attatcacgc ttcttnttct ctactcgtca acatccaaca c         51

<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 19
cagaaccaag aacttttctg acctcntcct gtttcttccc ctaagtgcca g         51

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 20
tcgttcacaa ttctacctta tgacanggtc agaaacagaa catagtagat g         51

<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 21
attattatct tccatattaa atacangttt cctttgttgg ggctcagaaa a         51

<210> SEQ ID NO 22
<211> LENGTH: 51
<212> TYPE: DNA
<213> ORGANISM: Homo sapiens

```
<220> FEATURE:
<221> NAME/KEY: misc_feature
<222> LOCATION: 26
<223> OTHER INFORMATION: n = c or t

<400> SEQUENCE: 22
gaaaaatcca tcactttcct atatantagc aataaacatg tggaatttga a        51

<210> SEQ ID NO 23
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = null or a

<400> SEQUENCE: 23
ggcaacaaga gtgaaacttc atctcnaaaa aaaaaaaaa aaaaagctga a         51

<210> SEQ ID NO 24
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 24
cacaggttgt ggtgagccga gatccntcca ttgtactcat tgcattccag c        51

<210> SEQ ID NO 25
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or c

<400> SEQUENCE: 25
gcacaggttg tggtgagccg agatcnttcc attgtactca ttgcattcca g        51

<210> SEQ ID NO 26
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = g or t

<400> SEQUENCE: 26
aaaaccaaac caaagactga gaaatnatta gaagccactg gaagtttttt a        51

<210> SEQ ID NO 27
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 27
atttatccaa atgcctttcc atggcnttca ctgagcaaat tctggatttt t        51
```

```
<210> SEQ ID NO 28
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or t

<400> SEQUENCE: 28
tttccatgta gacagaagaa tgaggngcta ccctagtgtg tcccttaatg a          51
```